United States Patent
Miller et al.

(10) Patent No.: US 6,957,160 B2
(45) Date of Patent: *Oct. 18, 2005

(54) METHOD AND SYSTEM FOR REGISTERING PRE-PRODUCED WEBS WITH VARIABLE PITCH LENGTH

(75) Inventors: Charles Phillip Miller, Cincinnati, OH (US); Michael Sulya Kolodesh, Deerfield, OH (US); Daniel Jon Amundson, West Chester, OH (US); Mark Edward Southman, West Chester, OH (US); Jon K. McLaughlin, Lebanon, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/731,807

(22) Filed: Dec. 9, 2003

(65) Prior Publication Data

US 2005/0125180 A1    Jun. 9, 2005

(51) Int. Cl.⁷ .......................... G01C 17/38; G01P 21/00
(52) U.S. Cl. ........................................................ 702/94
(58) Field of Search .............................. 702/94, 85, 127; 156/64, 324; 900/122, 124, 125

(56) References Cited

U.S. PATENT DOCUMENTS

| | | | |
|---|---|---|---|
| RE30,904 E | | 4/1982 | Miller et al. |
| 4,528,630 A | * | 7/1985 | Sargent ..................... 700/125 |
| 4,540,595 A | | 9/1985 | Acitelli et al. |
| 4,549,917 A | | 10/1985 | Jensen, Jr. |
| 4,610,739 A | * | 9/1986 | Jensen ......................... 156/64 |
| 4,680,205 A | | 7/1987 | Lerner et al. |
| 4,695,278 A | | 9/1987 | Lawson |
| 4,795,454 A | | 1/1989 | Dragoo |
| 4,837,715 A | | 6/1989 | Ungpiyakul et al. |
| 5,045,135 A | | 9/1991 | Meissner et al. |
| 5,094,708 A | | 3/1992 | Bechtel et al. |
| 5,151,092 A | | 9/1992 | Buell et al. |
| 5,156,793 A | | 10/1992 | Buell et al. |
| 5,221,058 A | | 6/1993 | Fillis |
| 5,235,515 A | | 8/1993 | Ungpiyakul et al. |
| 5,286,543 A | | 2/1994 | Ungpiyakul et al. |
| 5,359,525 A | | 10/1994 | Weyenberg |

(Continued)

FOREIGN PATENT DOCUMENTS

WO    WO 96/29966 A1    10/1996

(Continued)

*Primary Examiner*—Bryan Bui
*Assistant Examiner*—Demetrius Pretlow
(74) *Attorney, Agent, or Firm*—Jack L. Oney, Jr.; Ken K. Patel; Steven W. Miller

(57) ABSTRACT

A new machine control method and system for registering pre-produced webs into a converting line producing disposable absorbent articles such as diapers, pull-ups, feminine hygiene articles or a component thereof. The pre-produced webs can include a multiplicity of pre-produced objects spaced on the web at a pitch interval in the web direction. The pre-produced web being manipulated in order for the pre-produced object of the web to be registered in relation to a target position. The present invention includes five embodiments, where the first embodiment is expressed as a generic claim. The first embodiment includes a closed-loop feedback registration system; the second and third embodiments, in addition, include an open-loop feedforward control system; the fourth and fifth embodiments, in addition, include an automatic phasing system. In addition, the third embodiment uses a machine vision system to recognize any element of a complex pre-produced object (e.g., colorful graphics).

6 Claims, 15 Drawing Sheets

U.S. PATENT DOCUMENTS

| | | | |
|---|---|---|---|
| 5,483,893 A | 1/1996 | Isaac et al. | |
| 5,486,254 A * | 1/1996 | Gallagher et al. | 156/229 |
| 5,518,801 A | 5/1996 | Chappell et al. | |
| 5,569,234 A | 10/1996 | Buell et al. | |
| 5,659,538 A | 8/1997 | Stuebe et al. | |
| 5,665,151 A | 9/1997 | Escano et al. | |
| 5,722,178 A | 3/1998 | Wells | |
| 5,766,389 A | 6/1998 | Brandon et al. | |
| 5,932,039 A | 8/1999 | Popp et al. | |
| 5,964,970 A | 10/1999 | Woolwine et al. | |
| 5,980,087 A | 11/1999 | Brandon et al. | |
| 6,033,502 A | 3/2000 | Coenen et al. | |
| 6,074,333 A | 6/2000 | Rajala et al. | |
| 6,086,694 A * | 7/2000 | Winter et al. | 156/64 |
| 6,245,168 B1 | 6/2001 | Coenen et al. | |
| 6,354,984 B1 * | 3/2002 | Hensley et al. | 493/11 |
| 6,404,910 B1 | 6/2002 | Ungpiyakul et al. | |
| 6,444,064 B1 | 9/2002 | Henry et al. | |
| 6,533,268 B2 * | 3/2003 | Williams et al. | 271/228 |
| 6,615,408 B1 | 9/2003 | Kaiser et al. | |
| 6,743,314 B2 * | 6/2004 | Henry et al. | 156/64 |
| 6,764,563 B2 * | 7/2004 | Henry et al. | 156/64 |
| 2003/0010455 A1 * | 1/2003 | Henry et al. | 156/363 |
| 2003/0136495 A1 | 7/2003 | Miller et al. | |
| 2004/0051059 A1 * | 3/2004 | Ungpiyakul et al. | 250/559.29 |

FOREIGN PATENT DOCUMENTS

| | | |
|---|---|---|
| WO | WO 97/24094 A1 | 7/1997 |
| WO | WO 97/25283 A1 | 7/1997 |
| WO | WO 99/32285 A1 | 7/1999 |
| WO | WO 00/40196 A1 | 7/2000 |
| WO | WO 00/59428 A1 | 10/2000 |
| WO | WO 00/59429 A1 | 10/2000 |

* cited by examiner

METHOD AND SYSTEM FOR REGISTERING PRE-PRODUCED WEBS WITH VARIABLE PITCH LENGTH

FIELD OF THE INVENTION

The present invention relates to a method and system for registering pre-produced webs to a converting line producing disposable absorbent articles.

BACKGROUND OF THE INVENTION

In the manufacture of disposable absorbent articles such as diapers and feminine hygiene, it is a common manufacturing practice to combine continuously moving webs. These webs are typically represented by plastic films, nonwovens, elastics, etc. supplied to a converting line in their original production form and do not require special positioning before combining with other materials on the converting line. However, the manufacture of disposable absorbent articles may benefit if the above materials are supplied to the converting line as pre-produced materials, i.e., produced off the converting line and carrying various elements of disposable absorbent articles consecutively spaced along the web length at a nominal pitch length. Because the pitch length between the consecutively spaced elements of the pre-produced materials can vary at small but significant variations, commonly understood as random disturbances, in order to ensure consistent positioning of the product elements in every absorbent article, there is a demand for a method to register the consecutively spaced pre-produced elements in relation to desired positions, combining the pre-produced materials into a final article or product.

For example, a pre-produced breathable polymer film made off the converting lines that are particularly useful as backsheet materials for disposable absorbent articles typically have good surface characteristics that make them suitable for the application of multi-colored, high resolution graphics, but such films tend to be mechanically unstable with a particular tendency toward thermal shrinkage in the machine direction, commonly understood as a steady state disturbance. Such instabilities contribute to the difficulty in correctly positioning the pre-produced objects (e.g. graphics) on the polymer web in relation with a desired, target position on a disposal absorbent article. Various methods and apparatus have previously been used for combining components having random disturbances. For example, in conventional "discrete phasing" operations, the product is built around the pre-produced object, by adjusting the timing position of the machinery in response to a correction signal. However, it cannot be used in operations where in webs having steady state disturbance described above. See, e.g., International Publication No. WO 96/29966, and U.S. Pat. No. 5,659,538.

In "non-continuous web placement" operations, the pre-produced web is discretized, or cut, into segments. Each segment is then placed on the target web or product in the desired position. This does not, however, ensure the centering of the pre-produced object on the target web; furthermore, it limits the overall product design. The length of the discretized segments must be less than the length of the product, which may allow leakage in the areas where the product is longer than the discretized segment, for example, in the waist region of a diaper.

Other control systems and apparatus for registration have been described; see International Publications WO 97/24094 and WO 97/24283. However, none of the existing systems or apparatus for registration addresses a system in which inherent significant material instabilities exist, nor do they address a system in which the pitch length of the pre-produced object is non-uniform, particularly if the pre-produced pitch length is longer than the pitch length of the product under production. Similarly, a control system such as that disclosed in U.S. Pat. No. 5,766,389 requires a fixed target pitch. In practice, the target pitch can be subject to the same instabilities as that of the pre-producing webs.

Based on the foregoing, there is a need for a system for registering pre-produced webs having variable pitch lengths, at least one of which has consecutively spaced pre-produced objects. Furthermore, there is a need for a registration control system that can account for the material specific instabilities that inherently exist in such webs and that present small but significant variations resulting there from, which make it difficult to work (e.g., combine) such webs. There is also a need for a system in which registration of incoming webs having either longer or shorter pitch lengths than the pitch length of the product under production is possible. In addition, there is a need for a system in which automatic phase control is needed for the combination of the random pitch disturbance and steady state disturbance which result in a mean shift in the pre-produced pitch around a target pitch length which make it difficult to work such webs. None of the existing systems provides all of the advantages and benefits of the present invention.

SUMMARY OF THE INVENTION

In response to the difficulties and problems discussed above, a new machine control method and system for registering pre-produced webs into a converting line producing disposable absorbent articles such as diapers, pull-ups, feminine hygiene articles or a component thereof, the pre-produced webs can include a multiplicity of pre-produced objects spaced on the web at a pitch interval from each in the web direction, the pre-produced web being manipulated in order for the pre-produced object of the web to be registered in relation to a target position constant provided. The registration method of the present invention may include the following steps of:

a. providing a controlled web having pre-produced objects spaced at a controlled pitch interval, wherein the controlled web being provided at a controlled velocity in a machine direction;

b. providing an actual bias position of the pre-produced object on the controlled web by detecting the pre-produced object with a sensor within a manufacturing cycle of a pitched unit operation;

c. providing the target bias position at a desired position within a manufacturing cycle of the pitched unit operation;

d. generating a correction signal based upon the actual bias position data and the target bias position constant;

e. adjusting the controlled velocity of the controlled web in order to register the pre-produced object of the controlled web in relation to the target bias position constant;

f. coupling the pitched unit operation with a controlled web metering point by providing a converter position reference signal fed forward from the pitched unit operation functioning as an independent axis to the controlled web metering point functioning as a dependent axis in order for the pre-produced object of the controlled web be in phase automatically with the pitched unit operation; and g. adjusting the target position in order to phase the actual position based on the controlled web bias.

Alternatively, the registration method of the present invention may include the following steps of:
a. providing a controlled web having pre-produced objects spaced at a controlled pitch interval, wherein the controlled web being provided at a controlled velocity in a machine direction;
b. providing an actual bias position of the pre-produced object on the controlled web by detecting the pre-produced object with a sensor within a manufacturing cycle of a pitched unit operation;
c. providing the target bias position at a desired position within a manufacturing cycle of the first pitched unit operation;
d. generating a correction signal based upon the actual bias position data and the target bias position constant;
e. adjusting the controlled velocity of the controlled web in order to register the pre-produced object of the controlled web in relation to the target bias position constant;
f. coupling the first pitched unit operation with at least one controlled web metering point by providing a converter position reference signal fed forward from the second pitched unit operation functioning as an independent axis to the controlled web metering point functioning as a dependent axis in order for the pre-produced object of the controlled web be in phase automatically with the first pitched unit operation;
g. inferring the pre-produced object pitch from the registration control loop output and using feedforward gain to automatically adjust a target phase offset position of the second pitched unit operation in order to compensate for variations in the pre-produced object pitch and to maintain the proper phase relationship.

The present invention includes five embodiments, where the first embodiment is expressed as a generic claim, and the four other embodiments include elements of the first, generic embodiment. The first embodiment includes a closed-loop feedback registration system; the second and third embodiments, in addition, include an open-loop feedforward phasing system, the fourth and fifth embodiments, in addition, include an automatic phasing system. The first, second, fourth and fifth embodiments include a sensor for detecting the position of the pre-produced objects on the web. However, the third embodiment uses for the sensing function a machine vision system capable of recognizing any element of a complex pre-produced object (e.g., colorful graphics).

These and other features, aspects, and advantages of the invention will become evident to those skilled in the art from a reading of the present disclosure.

BRIEF DESCRIPTION OF THE DRAWINGS

While the specification concludes with claims particularly pointing out and distinctly claiming the invention, it is believed that the present invention will be better understood from the following description which is taken in conjunction with the accompanying drawings, in which like designations are used to designate substantially identical elements, and in which:

DETAILED DESCRIPTION OF THE INVENTION

All references cited herein are incorporated herein by reference in their entireties. Citation of any reference is not an admission regarding any determination as to its availability as prior art to the claimed invention.

Definitions

As used herein, the following terms are defined as follows.

"Disposable absorbent article" means herein the following articles: a) baby articles including incontinence articles (such as disposable diapers, pull-ons, training pants), and other absorbent articles such as baby bibs; b) adult incontinence articles; and c) feminine hygiene articles.

"Machine direction" ("MD"), "web direction" or "web path" means the direction of movement of the product along a manufacturing line. The machine direction is shown in FIGS. 1, 5A, 5B, and 5C as an arrow labeled MD.

"Product pitch length" means the length of material, on a relaxed basis, that runs the full length of the product under production. A product pitch for typical diaper products is illustrated as "PP" in FIG. 2B.

"Manufacturing cycle," "machine cycle," or "production cycle" means herein a cycle of a pitched unit operation to make a single product. Manufacturing cycle can be expressed in various ways including degrees of a full circle represented from 0° to 360°.

"Registration process," "registration system," "registration," or "registering" means herein an automatic machine control process or system for introducing an offline pre-produced web, (which can have multiplicity of pre-produced objects spaced on the web at a pitch interval varying in the web direction) into a converting line producing disposable absorbent articles, by providing an automatic positional adjustment of the pre-produced object on the web, functioning as a controlled web metered by a dependent axis (e.g., a web metering point), to a target position constant associated with a pitched unit operation of the converting line.

Figure 1:
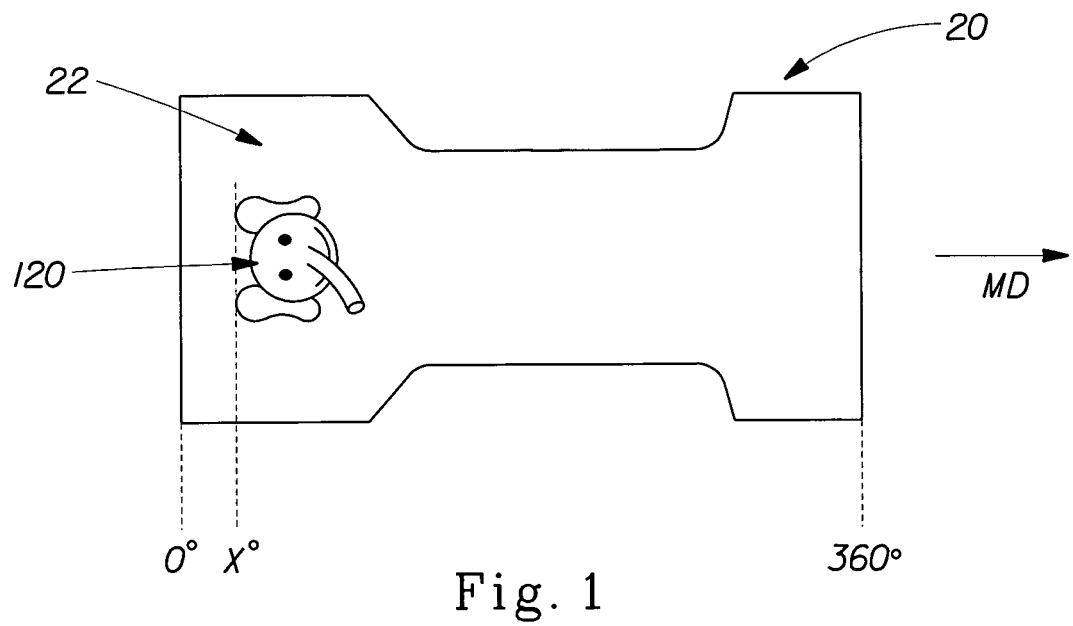
FIG. 1 is a plan view of an exemplary embodiment of a disposable diaper of the present invention in a flat, uncontracted position showing a desired location for a pre-produced object (e.g., graphic)

"Phase", "phase relationship", or "in phase" refers herein to a positional relationship between two or more axis of repetitive motion. The above terms can be expressed in a degree of rotation or in linear terms in the machine direction. For example, the phase representation from 0° to 360° for a flat, uncontracted diaper 20 is shown in FIG. 1. The phase position of an object can be described as any identifiable feature of the object. In FIG. 1, X° is representative of an exemplary desired phase position of the pre-produced object 22. "Phase" also refers to a change of a target position data or a setpoint variable of a controller.

"Registered graphics" refers to single or multiple colored graphic objects that can be printed on a web (an "off-line-made", "pre-produced" web) close to a specified pitch length on a relaxed web basis.

"Bias" refers to the amount of deviation a parameter has from its expected or nominal value "Feedback control" means herein a closed-loop electrical control method or a system for controlling the movement of an axis, wherein the closed loop includes functions of comparing input to output parameters.

"Feedforward control" means herein an open-loop electrical control method or a system for controlling the movement of a dependent axis from an input provided by an independent axis in a form of a signal expressed in a calculated mathematical relationship, into a controller of the dependent axis.

"Independent axis" can be a unit operation that can control one or more other unit operations, functioning as a master axis. Independent axis can be a pitched or a non-pitched unit operation. However, it should be understood that the independent axis can be also controlled by another independent axis. For example, in production of disposable absorbent articles, a combining unit can be controlled by an initial knife unit (for cutting a continuous material into discrete absorbent cores) and can at the same time function as an independent unit for controlling a web metering point unit (metering a controlled web).

"Dependent axis" can be a unit operation functioning as a slave axis controlled by an independent axis. Dependent axis can be a pitched or non-pitched unit operation.

"Target web" or "independent web" is an on-line-made web, which includes a multiplicity of targets objects spaced in the machine direction. An example of a target web can include a web containing absorbent cores spaced longitudinally along the web.

"Target object" means any object on the target web or a target position of the pitched unit operation, related to the manufacturing of the product, made on-line on the converting line, being spaced longitudinally at a pitch interval.

"Target web pitch length" means the nominal repeat length longitudinally, in the machine direction between consecutively spaced target objects on the target web.

"Pitched unit operation" refers herein to a MD fabrication apparatus having a pitch related function for working one or more webs in the manufacture of disposable absorbent articles, a portion, or a component of a disposable absorbent article. For example, the unit operation can include, but is not limited to such pitched web working apparatuses as a severing or cutting device, an embossing device, a printing device; a web activator (e.g., incremental-stretch activation devices disclosed in U.S. Pat. No. 5,151,092 to Buell et al.; U.S. Pat. No. 5,156,793 to Buell et al., and U.S. Pat. No. 5,518,801 to Chappell et al.), a discrete patch placing device (e.g., a cut-and-slip unit), a web combining device, and the like, all of which have in common that they include a manufacturing cycle corresponding to a product pitch length (e.g. a circumference or a trajectory movement of a rotary cutting device, a combining device and the like).

"Actual position data" means an actual position value within the machine cycle of a pre-produced object on a moving web; the pre-produced object being sensed to provide the position data once per the manufacturing cycle to the registration control system of the present invention.

"Actual bias position data" means an actual bias position value within the machine cycle of a pre-produced object on a moving web, the pre-produced object being sensed via a machine vision system to provide the position data once per the manufacturing cycle to the registration control system of the present invention.

"Target position constant" means a constant position value provided to the registration control system associated with the machine cycle. The target position constant can be any desired or selected position within the manufacturing cycle.

"Target bias position constant" means a constant position reference value provided to the registration control associated with a machine vision system. The target bias position constant can be any desired or selected position within the manufacturing cycle.

"Controlled web", "off-line-made", or "pre-produced web" means a web to be introduced into a converting line producing disposable absorbent articles, the web containing a multiplicity of pre-produced objects which are spaced at a pitched interval in the web direction; the controlled web can be manipulated (extended or contracted) by the control method of the present invention as needed to register the pre-produced object on the web in relation to a desired target position constant.

Figure 8:
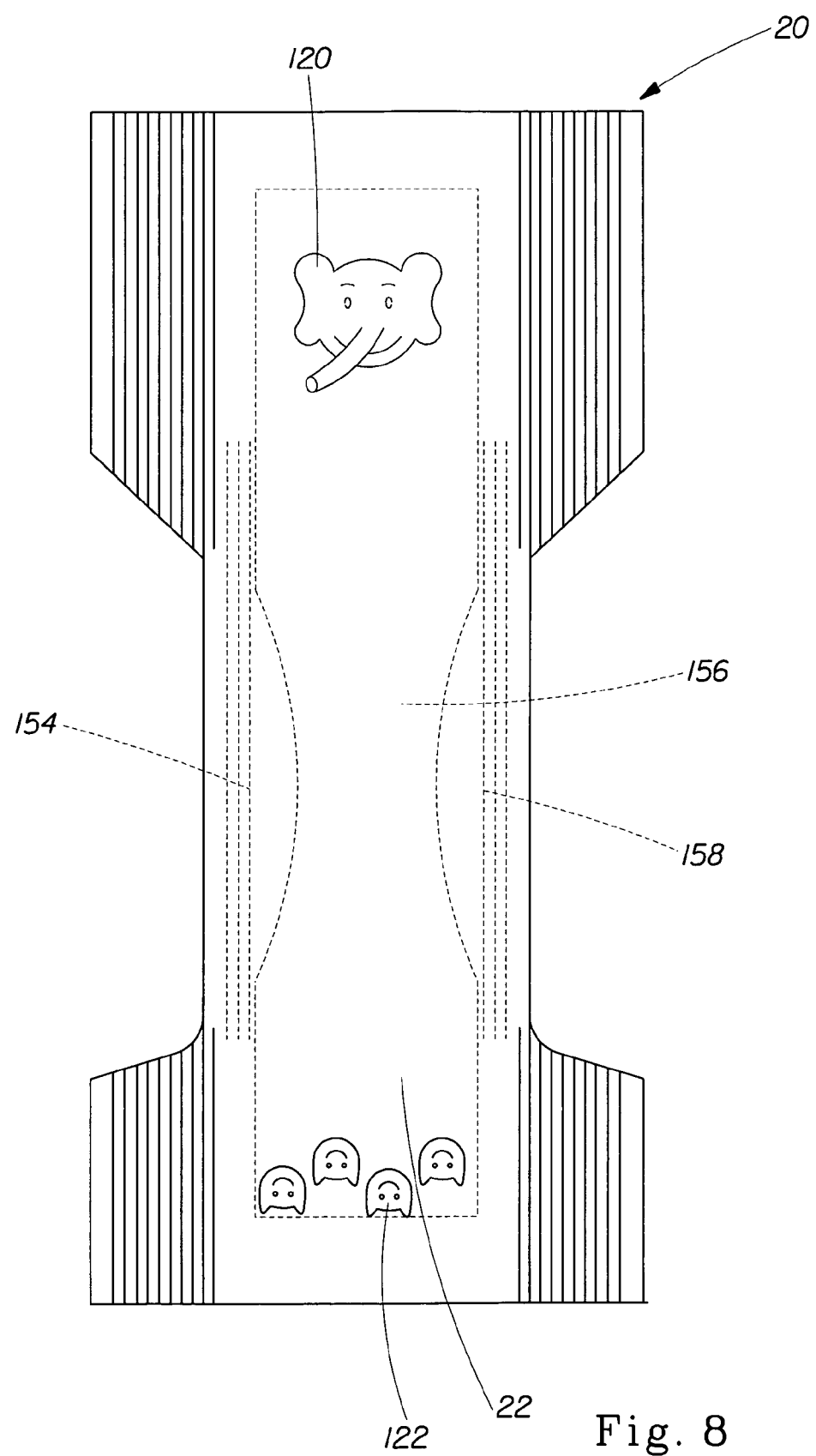
FIG. 8 is a simplified plan view of another exemplary embodiment of a disposable absorbent article having registered graphics.

"Pre-produced object" herein means the pre-produced object on a web produced off the converting line on a separate independent process not control-linked to the process of the converting line, and spaced at a pitch intervals in the web direction. The term "pre-produced object" as used herein refers to any object or physical property, visible or normally invisible to the human eye, pre-bonded, pre-applied, pre-cut, pre-glued, pre-activated, pre-embossed, or any combination thereof within a single product pitch Lpp., For example, a pre-produced object 22 comprising of graphics 120 and 122 of a disposal article, (as shown in FIG. 8)

of disposable absorbent articles. Furthermore, the term "pre-produced object" also can refer to a registration mark specifically provided for the purpose of registration. The registration mark may be both visible and normally invisible to the human eye.

"Controlled web pitch length" means the repeat length in a machine direction (MD) between consecutively spaced pre-produced objects on the controlled web.

The term "image" refers herein to a representation of a pre-produced object, a combination of pre-produced objects, a portion of the pre-produced object, a portion of the combination of pre-produced objects, generated electromagnetically, acoustically, or any combination thereof. It should be understood that the tern "image" can include areas surrounding the pre-produced object.

The present invention is directed to a process for registering off-line made pre-produced webs in relation to a target position on a disposable absorbent article. The pre-produced objects on a web spaced at pitched intervals which include variations or disturbances may result, for example, from virtual impossibility to maintain a constant web tension during pre-producing (due to machine variations) and then in a roll form (due to inherent tension differential among web layers of the roll), as well as climatic conditions affecting, for example, mechanically unstable microporous polymer films during storage.

It is noted that any other polymer films, non-woven or woven webs, etc. capable of stretching under a tension force applied along the web path, can be useful as controlled webs herein. It is also noted that although the description of embodiments contained herein is primarily given in the context of a diaper converting line, i.e., registration of pre-produced objects phased to diaper cores or a pitched unit operation (target objects) on a diaper converting line, it will be understood by those of skill in the art that the registration process herein may be used to register webs in any application.

Where webs each carrying phased objects must be combined in a predetermined relationship, information pertaining to the phase position of the target web, usually the product under production, e.g., the diaper chassis assembly, must be fed to the web handling process. In addition, the position of the phased objects (e.g., a pre-produced object, such as a pre-produced graphic or a registration mark on a polymer backsheet web or a non-woven topsheet) on each incoming, controlled web which is to be combined with the target web must also be known and fed. As previously noted, the target web pitch length and the controlled web pitch length are rarely identical. It will be understood by those of skill in the art that any incoming fed web may be designated as a target web or a controlled web, and processed accordingly.

The continuous registration system of the present invention performs two functions simultaneously in order to correctly register pre-produced webs to a target position. First, it continuously corrects the pre-produced pitch length, or spacing of the pre-produced objects on the controlled web, to match the pitch length of the target object. Second, it continuously synchronizes the phase positions of the two such that they are combined in the proper position, e.g., such that the graphic 22 is correctly located as desired on the diaper 20, for example, in substantially the positions shown in FIG. 1, 7 or 8.

Figure 2A:
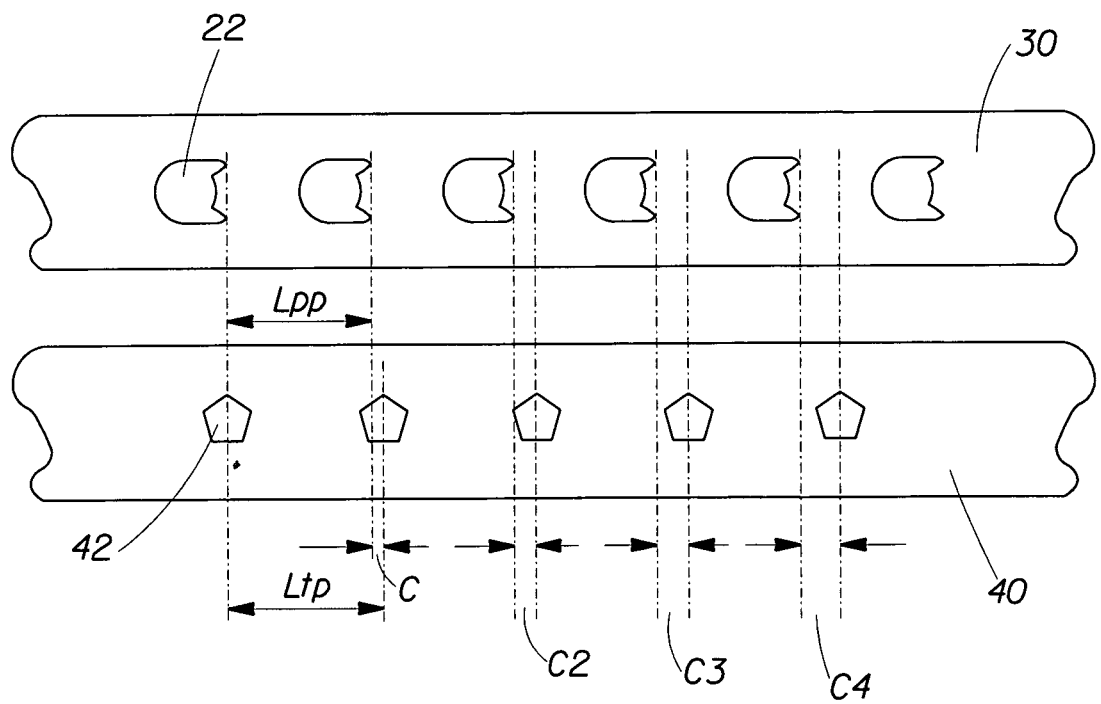
FIG. 2A is a schematic diagram showing simplified representations of a portion of a continuous diaper backsheet web having consecutively spaced pre-produced objects (e.g., pre-printed graphics) thereon and a portion of a diaper product web.
Figure 2B:
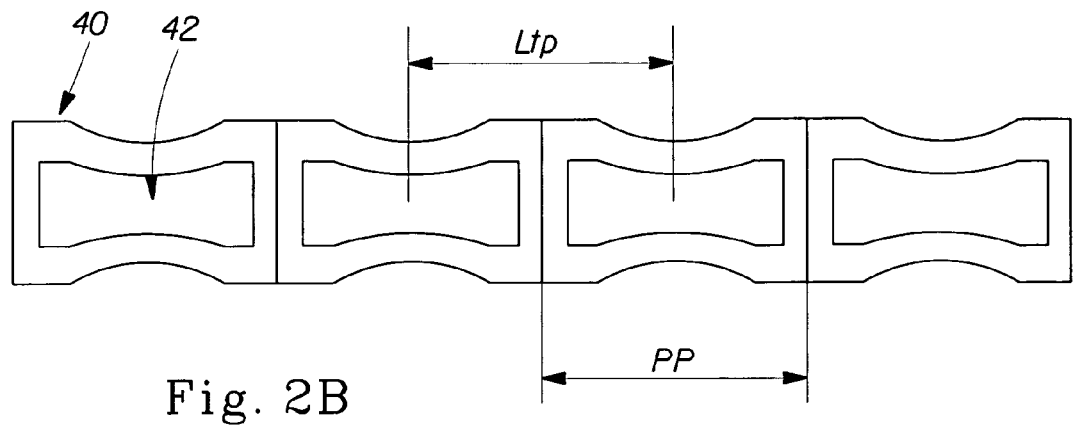
FIG. 2B is a top view of a diaper product web including a representation of the diaper core area.
Figure 5A:
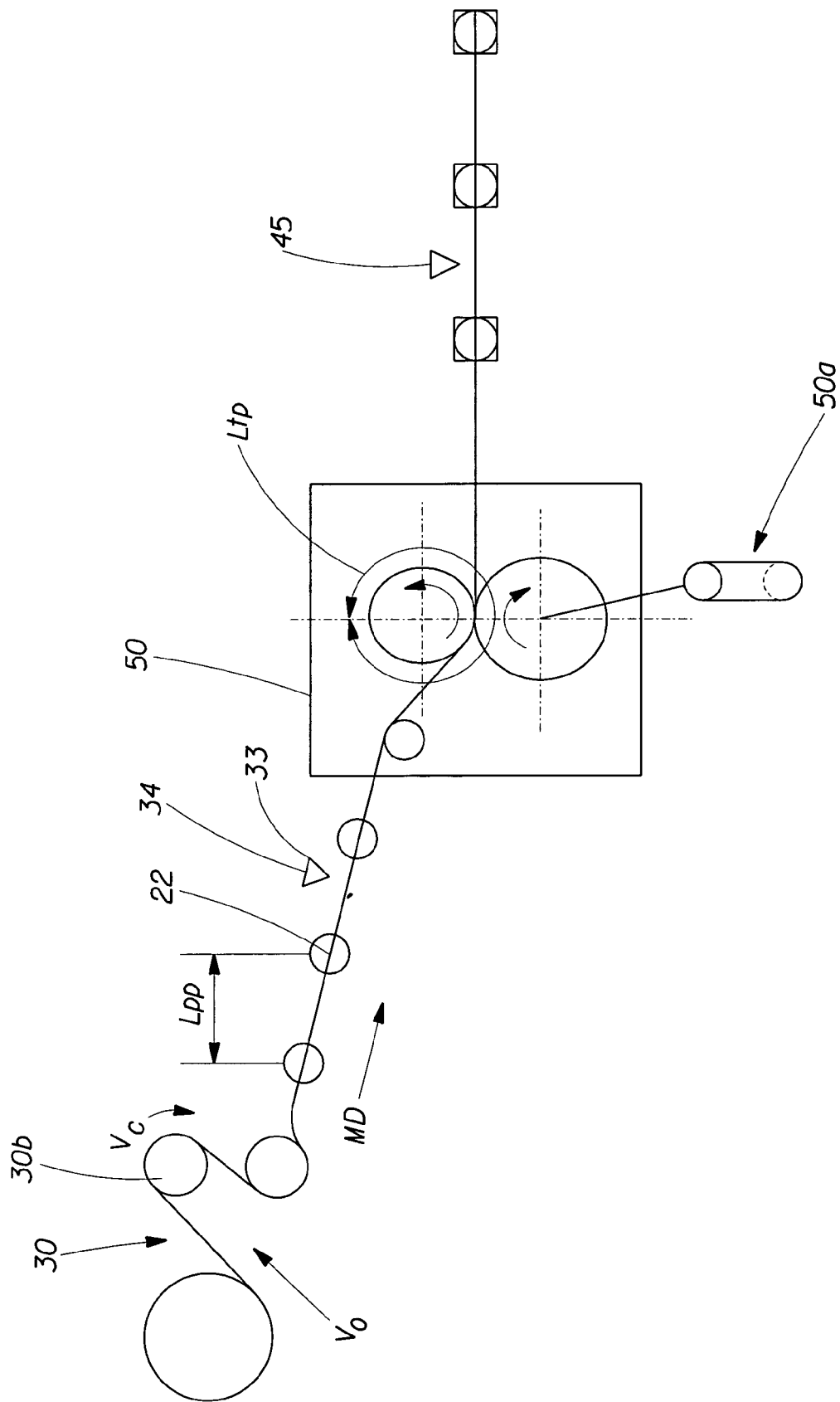
FIG. 5A is a schematic diagram of a first embodiment showing the process of registering one printed web to a pitched unit operation.
Figure 5B:
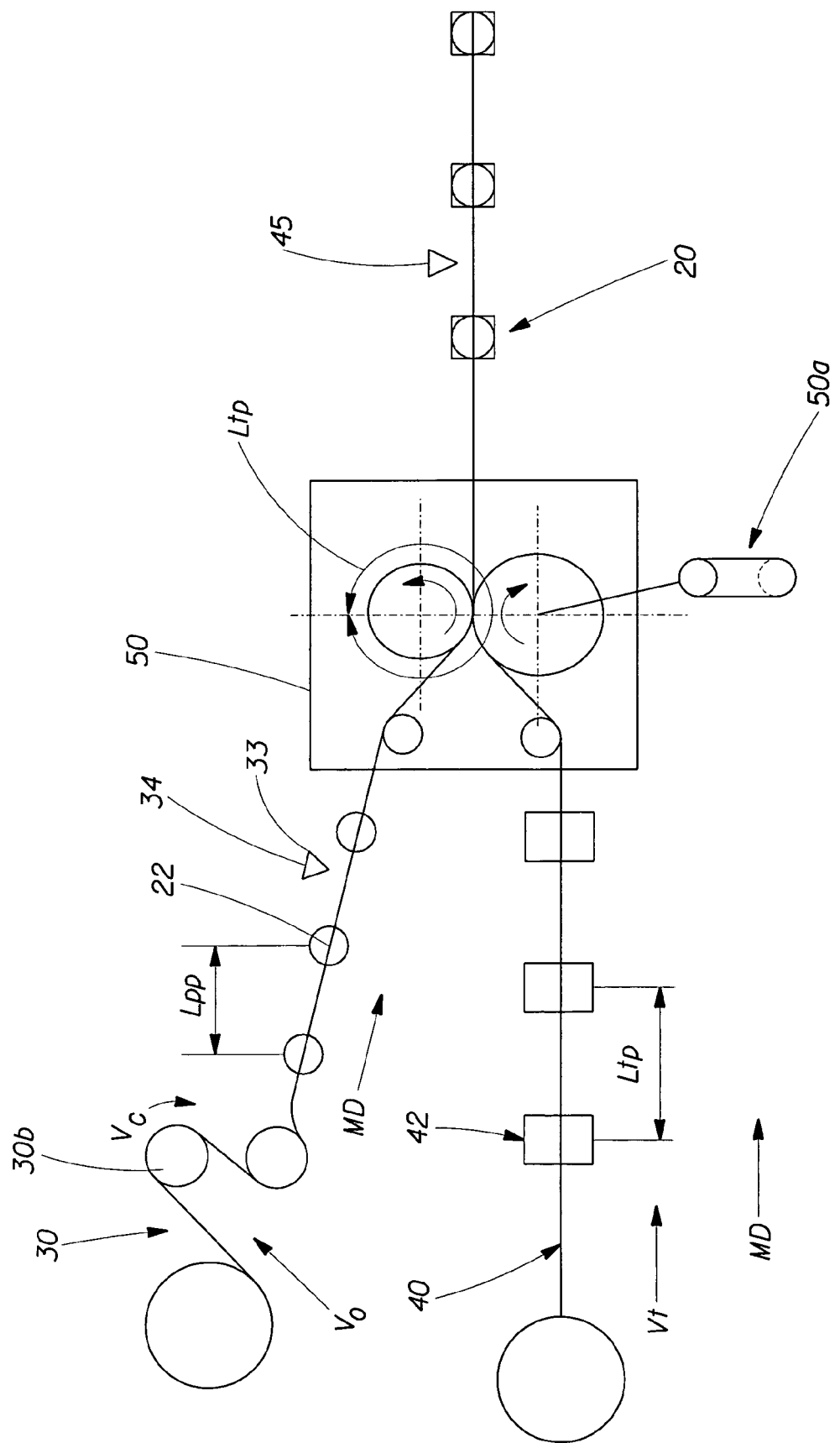
FIG. 5B is a schematic diagram of a second and fourth embodiment of the present invention showing the process of combining two simultaneously advancing webs.
Figure 5C:
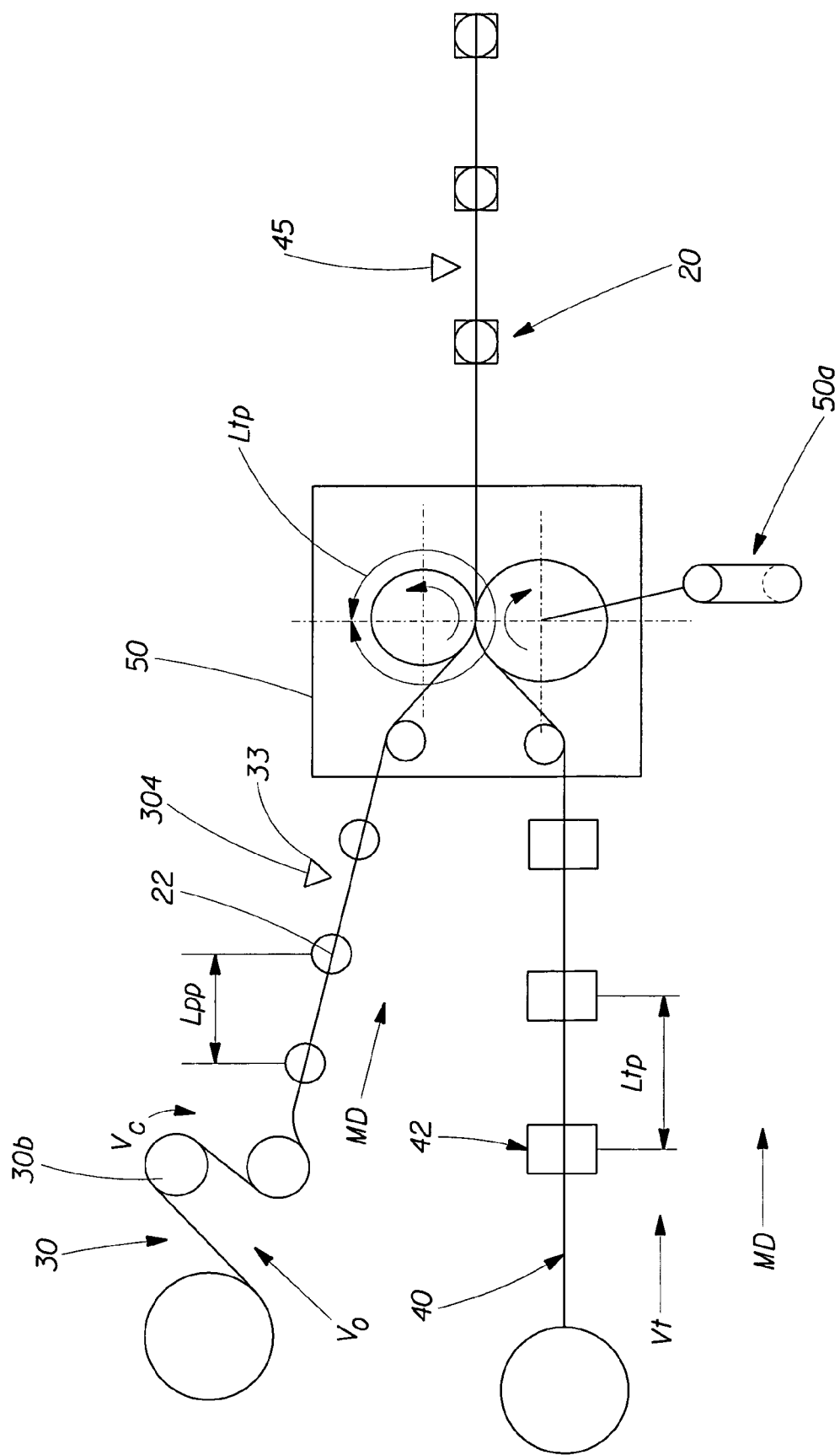
FIG. 5C is a schematic diagram of a third embodiment of the present invention showing the process of combining two simultaneously advancing webs.

The target object can comprise that part of the diaper chassis itself that is generally continuously comprised of the core and topsheet assembly, prior to the attachment of the backsheet web. FIGS. 2A and 2B show a target web 40 including target objects 42 consecutively but not equidistantly spaced thereupon at a target web pitch length, "Ltp". FIGS. 5A, 5B, and 5C show the Ltp in two representations; the first one, as a pitch between target objects on the target web 40. One example of Ltp as a pitch between target objects 42 may be the pitch between the absorbent cores on the target web 40, and another example may be a circumference of a rotating element working the web of the pitched unit operation 50.

It is noted that the target object position may be directly sensed or inferred from the use of an electronic strobe. When the system is first started up, the operator inputs an offset value using an "advance/retard" button while examining the position of the controlled web graphic using an actual strobe light, reading the finished product, or using a vision system that is strobed once per product. Once the offset value is set, the registration system will target the controlled web pre-produced object to the same point in the machine cycle.

Again referring to FIG. 2A, the controlled web 30 may comprise a continuous film material, for example, a breathable microporous polymer film, that is used as part of the diaper backsheet. The controlled web 30 has pre-produced objects 22, consecutively but not equidistantly printed thereupon at a particular controlled web pitch length, "Lpp". Lpp is invariably something other (either longer or shorter) than both the product pitch length PP and the pitch length of the target web Ltp due to climatic conditions, thermally induced creep, and the like. An exemplary Lpp is shown in FIG. 2A. Pre-produced objects 22 may be registered graphics that are colorful, high resolution designs that are appealing to the consumer, who is typically a care-giver to the wearer of the diaper, or who in other cases may actually be the wearer.

As noted above, in most cases, Ltp is not equal to Lpp; in fact, exact matches are highly improbable. This difference is a major source of the difficulties associated with proper phasing of the controlled web 30 and the target web 40. As can be most clearly seen in FIG. 2A, a pitch delta C (e.g., Ltp minus Lpp) usually exists and must be corrected in order to insure proper product phasing. It is additionally noted that the pitch delta C associated with Ltp and Lpp typically accumulates for each subsequent target object 42, and thus a greater amount of correction is generally needed. This error accumulation of pitch delta is represented in FIG. 2A as C, C2, C3, C4.

The corrections of pitch delta C, C2, etc. associated with the registration system of the present invention may not actually be necessary for product functionality; however, they are critically important for consumer acceptance of the diaper products produced.

Figure 3:
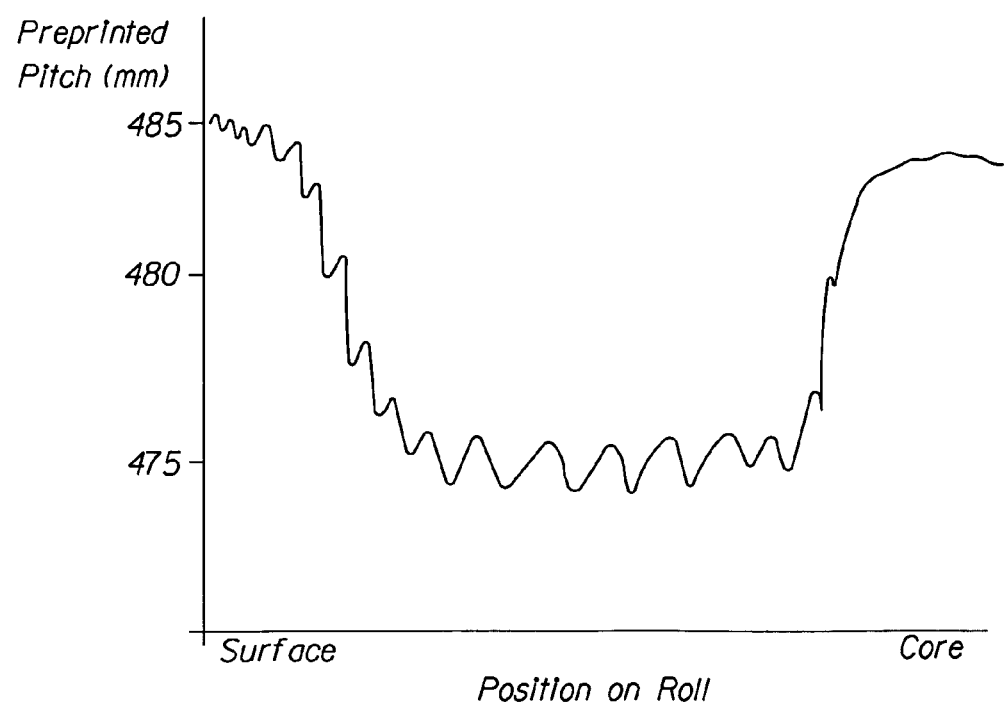
FIG. 3 is a graphical representation of the pitch length variation typically experienced by pre-produced microporous materials that have been subjected to typical conditions of winding and warehouse storage.

FIG. 3 illustrates the instabilities in controlled web pitch length Lpp that may arise due to the inherent thermal instability of the microporous polymer films of the present invention. Such thermal instability leads to differential shrinkage of the microporous film, and significant variations in Lpp frequently result. Referring to FIG. 3, the position along a wound roll (i.e., a continuous, controlled web 30) of microporous polymer film that has been pre-produced with registered graphics is represented on the X axis. The start of the roll is indicated at the origin of the axes, while moving to the right along the X axis indicates moving toward the core of the roll, corresponding to unwinding the roll.

On the Y axis, pre-produced pitch length Lpp is represented in millimeters. As can be seen, differences in pre-produced pitch lengths Lpp of up to about 10 mm may be seen between various locations on the same web of material.

The registration system of the present invention is thus designed to overcome the phasing problems associated with combining the target web 40 and the controlled web 30 where Lpp is not equal to Lpp, where Lpp is inherently variable, and where both webs are simultaneously and continuously fed to a combining operation. The process has the ability to on-goingly adjust the pitch length of the controlled web 30 as delivered to match or to more closely approximate that of the target web 40. In addition, the system of the present invention makes such correction in a gentle, non-abrupt and gradual fashion so as to account for the delicate nature of the web, which may be a microporous polymer film, without damaging it. Alternatively, if conventional higher strength webs are used, the system is capable of making more rapid and abrupt adjustments that may not be acceptable with the microporous polymer films.

As described more fully below, this is accomplished by the use of web tension transients to change the pre-produced pitch length Lpp of the pre-produced objects on the controlled web 30. Changing the tension in a web causes a change in the pitch length of the web. Thus, more tension stretches the material of controlled web 30, causing the pitch length Lpp to increase, while less tension relaxes the controlled web 30, causing the pitch length Lpp to decrease. The absolute tension in the controlled web 30 should not approach zero tension, as control of the controlled web 30 would be lost. Conversely, more or less web may be metered to the process, which also changes the level of tension in the web.

The system of the present invention thus introduces small tension transients, which provides on-going correction. This serves to maintain the integrity of the delicate, mechanically unstable polymer films that are useful for disposable absorbent articles herein. It also serves to correct the phase relationships of objects on the each incoming web in increments that are too small to be detected by the web handling process, which means that there is little possibility for the amount of error to become large enough to trigger the shut-down functions of the web handling process. In addition, it allows for manufacture of consecutive products that may have insignificant differences in the locations of the pre-produced objects on each product.

Any control algorithm that creates such small on-going transients is useful herein. The control system prepares small transient corrections in a timely fashion that intervene in the control of incoming web handling drives to prevent mismatches between the positions of the target object and the pre-produced object from drifting out of the zone that the consumer would find acceptable. Exemplary control algorithms herein include manual control, a control algorithm based on statistical process control, or a Proportional Integral (PI) control system.

It is believed that control systems relying on statistical analysis of past history such as running average are simply too sluggish to stay ahead of the significant variation observed in the position of pre-produced objects on the in-running controlled web 30. To avoid the complexity of controlling multiple drives to position the pre-produced object, an exemplary embodiment herein is a PI control algorithm which controls the feed rate of the controlled web 30 only as necessary to minimize the strobed distance between a fixed position of converter machine time with user-set offset and the sensed mark. If the space between the sensed marks of the controlled web 30 (Lpp), is longer than the target pitch length Ltp, more web 30 is fed to the process, reducing the web tension and allowing the space between pre-produced objects to contract. Conversely, if the space between the sensed marks of the controlled web 30 is too short, less web is fed, causing an increase in web tension causing the space between marks to increase. In this way, not only is the pitch of the web brought close to the pitch of the product, but the position of the pre-produced object is brought close to the target position.

Alternatively, where the pre-produced objects are made discrete through a cutting operation and then placed on the target web, the tension can be kept constant by varying the controlled web flow rate upstream from the cutting operation. In this case, the controlled web tension is not varied with the spacing of the sensed marks.

To determine the position of the pre-produced objects on controlled webs various detectors/scanners may be used, such as capable of detecting changes in electromagnetic or acoustic fields. For example, to determine the position of the pre-produced object (e.g., color graphic) on the incoming controlled web 30, a sensor is selected which detects differences between light passing through the web via different printed colors. The color of the target web object, the position of the target web object relative to other objects of the same color, and the size of the target object combine to create the means for generating a clean signal whose position is strobed once per machine cycle.

Alternative means of establishing position of pre-produced objects include: 1) sensing a visible timing mark on a part of the web that can be later removed by the process; 2) sensing a normally invisible to the human eye registration mark which may or may not remain a part of a final article or product; 3) using a grid of sensors to look for a recognized pattern of light diffusion or 4) using an array of sensors, as in a machine vision system to look for a recognized pattern contained in an electro-magnetically or acoustically generated image.

Figure 6A:
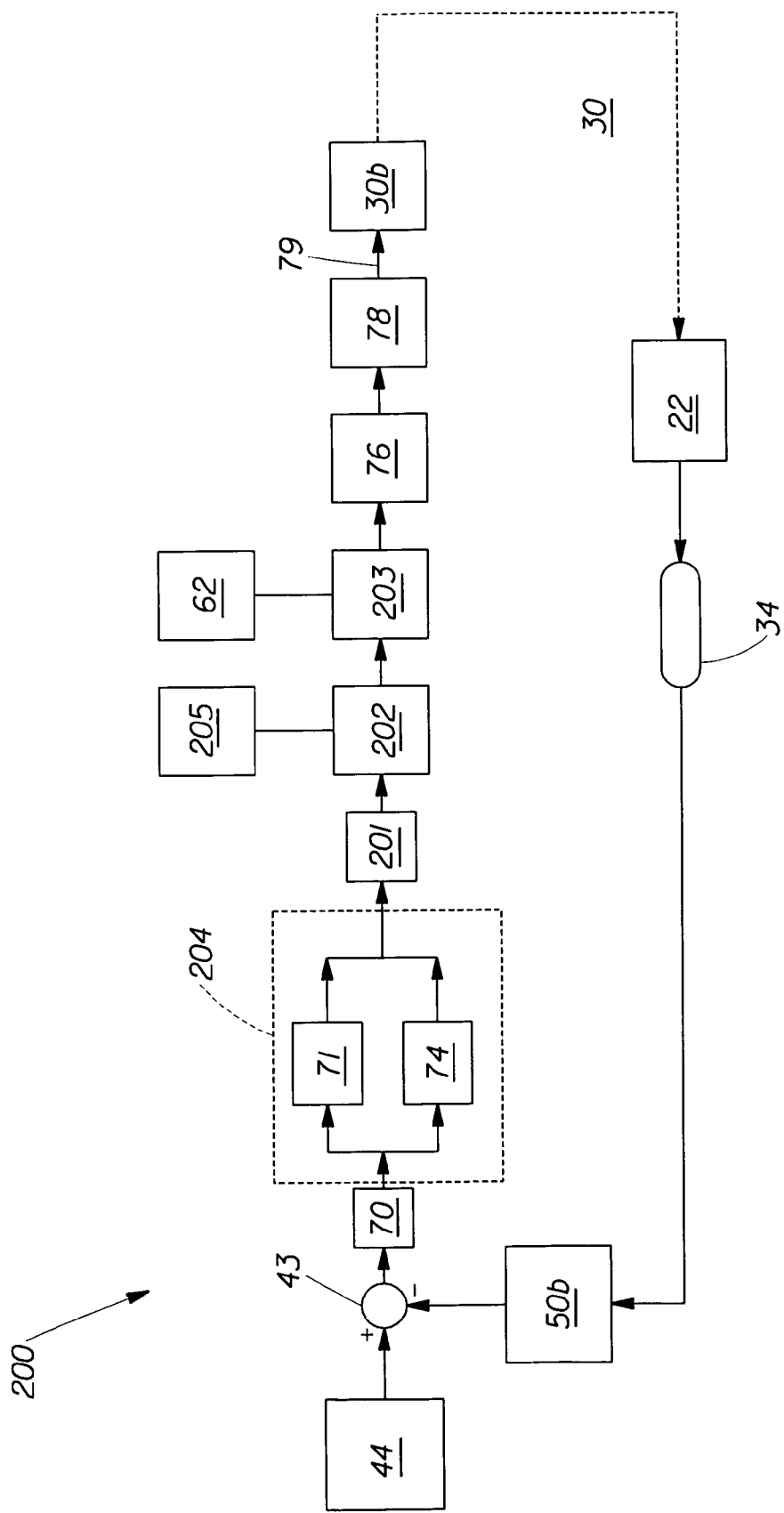
FIG. 6A is a block diagram of a first and second embodiment of the registration control system of the present invention.
Figure 6B:
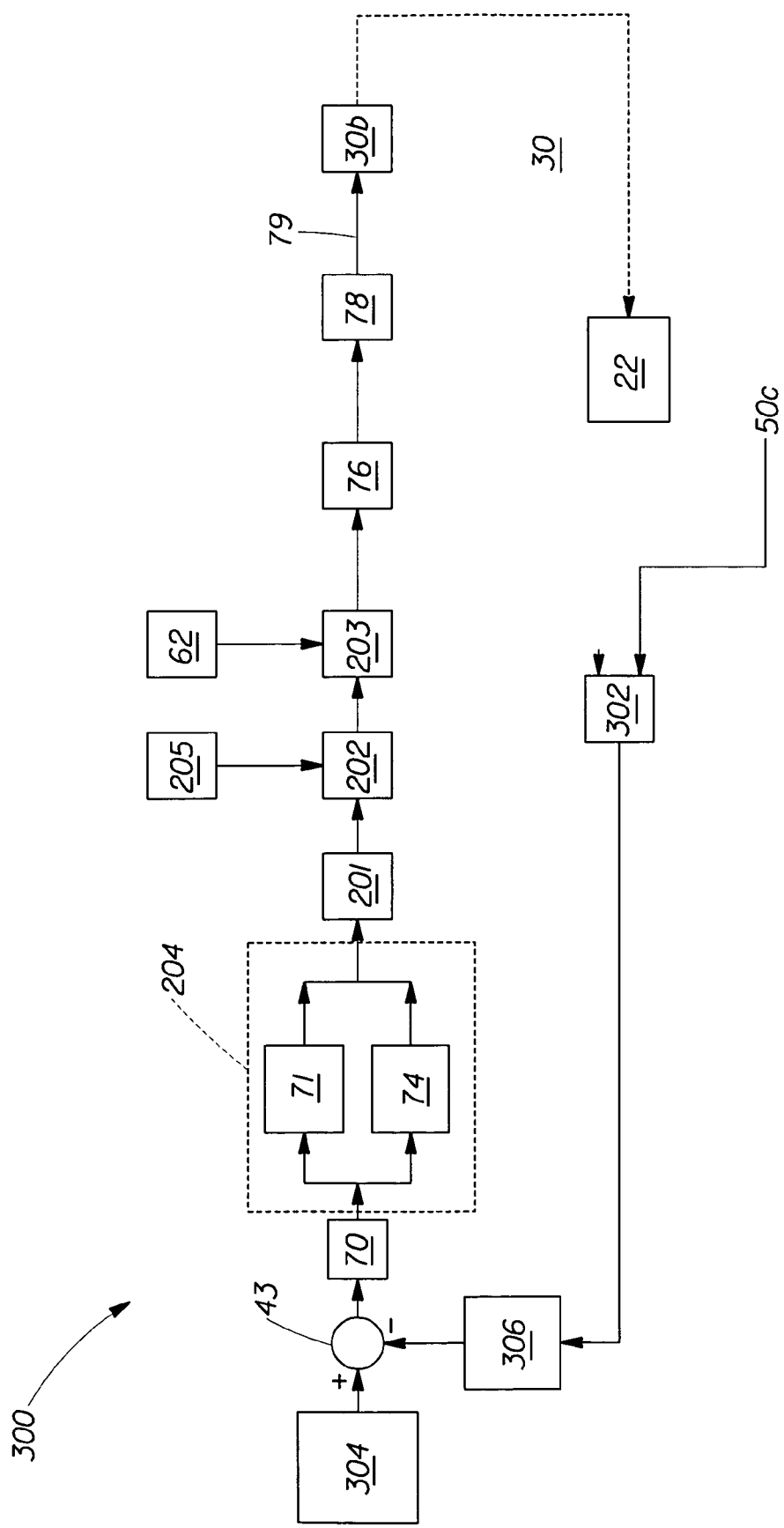
FIG. 6B is a block diagram of a third embodiment of the registration control system of the present invention.

The PI control system shown in FIGS. 6A and 6B seeks to minimize the error distance which is observed once per product. The proportional gain (Kp) 71 sends a correction signal to the controlled web feed drive that is proportional to the size of the error. The integral gain factor (Ki) 74 is set to eliminate the steady state offset typical of purely proportional control. It is observed in FIGS. 6A and 6B that the error signal trims the operation of the feed drive which is typically running at "gear ratio" relative to rate of product production. Although speed and position may vary, on average one pre-produced object must be processed per target product.

The registration system of the present invention may adjust the pitch Lpp of the controlled web 30 by on-goingly adjusting the tension in the controlled web 30. The Lpp is adjusted to "Lc", which is used herein to mean "length at combining." Lc is equal or approximately equal to Ltp, i.e., the pitch length of the controlled web 30 is made approximately equal to that of the target web 40 so that the pre-produced object 22, can be positioned in the correct phase relationship to the product. This tension acts through the web modulus, Ew, of the controlled web 30, according to the following equation:

$$Lc=(1+\epsilon) \times Lpp = (1+T/Ew) \times Lpp, \text{ where:}$$

$\epsilon$=strain;

T=controlled web tension; and

Ew=web modulus of controlled web.

The foregoing equation acts for all webs being combined together. Thus in the case of two webs:

$$Lc1=(1+T1/Ew1) \times Lpp1 \text{ and } Lc2=(1+T2/Ew2) \times Lpp2.$$

As noted above, at the point of registered combining under steady state conditions, Ltp is equal to Lc. Thus, the ratio of the relaxed lengths combined at any time is given by the equation:

$$Lc1/Lc2=(1+T2/Ew2)/(1+T1/Ew1).$$

The tension variables T as well as the modulus variables Ew each have a range of variation, so the ratio of the Lc values will always vary somewhat from unity. The difference between the Lc ratio and unity is referred to herein as "puckering":

$$\text{Puckering \%}=(Lc1/Lc2-1)\times 100.$$

The puckering value can assume positive or negative values depending which web has the least relaxed length. After the finished product is cut apart, the combined web is pulled to the length of the incoming web with the least relaxed length. This causes the other web to "pucker." Above a certain tolerance level, puckering has a noticeable impact on the appearance of the product. For a diaper backsheet formed from a nonwoven material and a polymer film pre-produced with pre-produced object designs, puckering levels up to about ±2%, while noticeable, are generally not perceived as distorting the appearance of the product.

Alternatively, different puckering levels can intentionally be created, or puckering may otherwise be controlled to create materials with different tactile feels as desired. Note that even below ±2% that puckering can be controlled and located on the product according to the present invention to minimize its impact on product appearance. To do this, the laminated material furthest away from the consumer is overfed and pulled back, thus hiding the puckering from the consumer.

The present invention has the capability of registering controlled webs having pitch lengths that are not uniform, and which can be either longer or shorter than the machine product pitch length. The ability to register materials with pitch lengths longer than the product under production allows the designer of such a product to tailor the surface texture of the product. This is demonstrated in FIGS. 4A and 4B, where two materials are laminated together by passing through a nip point. The material which is longer than the finished product pitch is pulled back by the other material. By making the layer of the laminate that is furthest away from the eye of the consumer the material that is pulled back, the impact of the registration process on the texture of the finished product is mitigated.

Figure 4A:
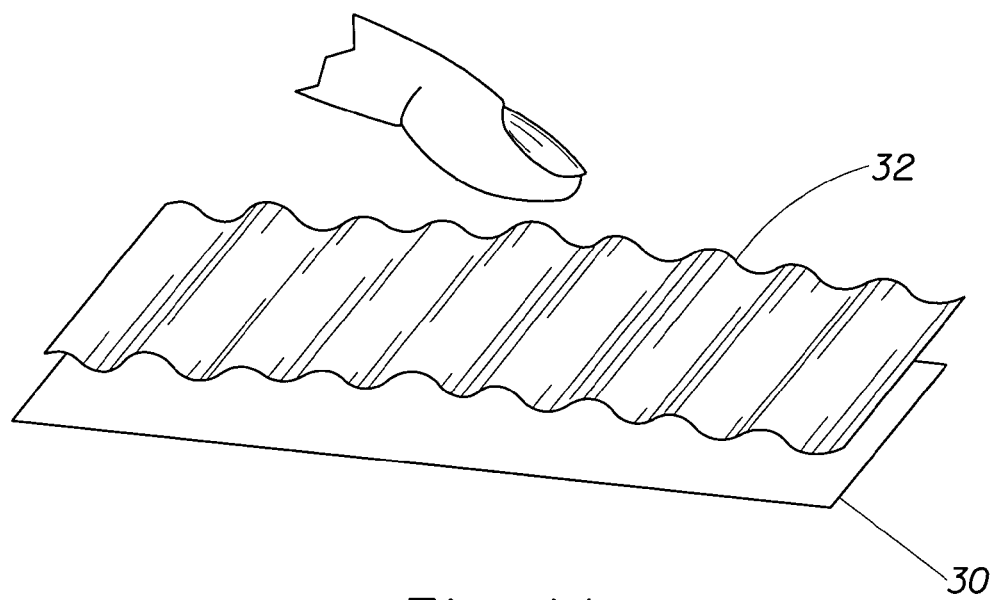
FIGS. 4A and 4B are perspective views of portions of exemplary embodiments of laminates of microporous material and nonwoven material, illustrating the impact of running the microporous material at a pitch length different from that of the nonwoven material.

In FIG. 4A, the pitch length of the nonwoven web 32 (Ltp) which may form a portion of the diaper backsheet is longer than the pitch length (Lpp) of the polymer film (controlled web) 30. In this case, after the final cut that separates the consecutive diaper products, the polymer film pulls back the nonwoven material. This creates a roughened texture on the exposed surface of the laminate which the consumer can see and feel.

Figure 4B:
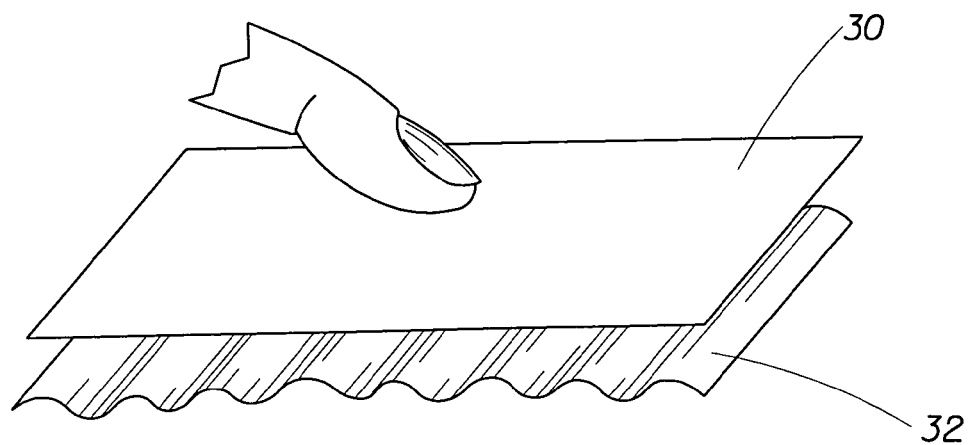

FIG. 4B shows the surface texture impact of the pitch lengths (Lpp) of the polymer film (controlled web) 30 longer than the pitch length (Ltp) of the nonwoven material web 32. In this case, the nonwoven material pulls back the polymer film material after the final cut. Thus, the impact of the unequal combining is manifested on the inside of the product and is hidden from the eye of the consumer. Thus, it may be desirable to overfeed the controlled web of polymer film material so that the consumer does not see or feel the roughened texture.

The nonwoven material 32 may be fed into the system as an independent web having phased objects with variable pitch length. In such a case, the nonwoven web and preferably the controlled web are phased as described herein, and combined; then the combination laminate material is phased and combined to the target web (diaper product web) as described herein.

Assuming that a puckering tolerance level of up to about ±2% is acceptable, the available adjustment rate for pre-produced objects is limited. It is important to design the registered printing such that a reasonable tolerance of pre-produced object position is accommodated. The pre-produced object position tolerance should be greater than or equal to the web to web position shift typically seen at the time of web splicing; that is, at the time that a subsequent roll of pre-produced web is supplied to the web combining process at the time that the previous roll is used up by the process. The roll to roll error is different and generally greater that the normal variation within a single roll. Thus, if random splicing were used, phasing corrections of up to 180 degrees (half of a full length) would sometimes be necessary. During such times, all product produced would need to be scrapped. The splice tolerances of the present invention are controlled in concert with the tolerances of pre-produced object position to reduce splice time rejected product to ideally zero (other than rejection of the splice tape itself).

The selection of the raw material to be used for the backsheet, i.e., the controlled web 30, may be constrained by both the product design and the registration system of the present invention. The key parameters that may be unique to pre-produced objects are impacted by the needs of product functionality. For diaper backsheet, an exemplary material is a breathable microporous polymer film. An exemplary microporous polymer film is formed from a mixture of polyethylene and calcium carbonate, and titanium dioxide if needed to increase the white appearance of the film, since whiteness is a film characteristic that is necessary for widespread consumer acceptance. In some instances, it may be desirable for the microporous polymer film to have high thermal stability characteristics in order to support the printing of high resolution color graphics thereon. It may be desirable that the film meets a maximum of ±1% repeat pitch variation, i.e., mismatch, but more typically ±2% is likely to be seen. It is believed that puckering ratios ranging from about 0.97 to about 1.015 may successfully be provided using this system, making it possible to handle films with an even wider range of pre-produced pitch length variation.

Other exemplary characteristics of the microporous polymer film that are important in assuring good processing with the registration system of the present invention include: web modulus (preferably from about 4000 to about 13,000); coefficient of friction (preferably high enough so that the system metering nips can act on the web with a sustainable level of web tension); and thermal enthalpy (preferably high enough to have sufficient heat resistance during hot melt glue lamination, but not increased to the point that the stiffness of the film increases to the point of discomfort for the wearer).

As previously noted, the process control dilemma that the registration system of the present invention must correct is two-fold.

First, pitch mismatch must be corrected. There is a difference in pitch between the pitched unit operation 50 (such as, e.g., a combining unit, a cutting device, an activator, and the like) and the pitch of the offline made web (controlled web 30). This difference in pitch is shown in FIGS. 2a, 5A, 5B, 5C, 5D as the difference between Ltp and Lpp, where Ltp−Lpp=pitch delta C. As described in connection with FIG. 2a, this pitch delta C accumulates as the number of products accumulates. Thus, for the first product, the pitch delta is about C; for the second product, the pitch delta is about C2; for the third product, the pitch delta is about C3, and so on.

Second, phase correction is needed. Phase error may be caused when a transient change occurs in the controlled web 30 via a controlled web splice or some phase upset in the position of the pre-produced object 22 in relationship to the target object 42 or the pitched unit operation 50 (such as, e.g., a combining unit, a cutting device, an activator, and the like).

FIRST EMBODIMENT

FIG. 5A shows a schematic diagram of the process of the first embodiment of registering the pre-produced web of the present invention. In the first embodiment, the registration system is a feedback control system requiring a comparison of an actual position of the pre-produced object 22 on the controlled web 30 to a target object position in relation to the finished product or the pitched unit operation 50. The controlled web 30 is initially fed at a velocity Vo, by a metering point 30b. The actual position data is provided by detection of the position of a pre-produced object 22 on the controlled web 30 moving in the machine direction MD, can occur automatically at a pre-produced object detection stage 33 via a sensor 34 which electronically strobes a resolver 50a providing actual position data 50b of the pre-produced object 22 (see FIG. 6A). A target position constant 44 (FIG. 6A) of the pre-produced object 22 is provided by an operator, which is a desired position value within the manufacturing cycle of the pitched unit operation 50. Alternatively, the target position constant 44 (FIG. 6A) of the pre-produced object 22 can be provided automatically via any suitable detection device capable of sensing the position of the pitched unit operation 50.

FIG. 6A shows a block diagram of a first embodiment of the registration control system 200 of the present invention. In the registration control system 200, a main reference signal is a converter velocity reference signal 62 of the pitched unit operation 50 that can be provided by an encoder 50a (see FIG. 5A), which provides a change of the converter position reference signal 62 of the encoder 50a over time (for example, one revolution of the encoder 50a per a target object 42). The converter velocity reference signal 62 is equal to the pitch length of the product times the converter rate. The converter velocity reference signal 62 is supplied to a feedforward (FF) control algorithm 203, to be multiplied with a gear ratio (GR) constant 202 in order to produce a servo velocity signal 76, which can be calculated by the formula below:

servo velocity signal=$GR$*converter velocity reference signal

Alternatively the converter reference signal 62 can be position based and can be used to generate a position based servo signal, utilizing the same control algorithm.

servo position signal=$GR$*converter position reference signal

The gear ratio (GR) 202 is a ratio of the nominal gear ratio of the pitched unit operation 50 ($NGR_{50}$) trimmed by a correction signal (u) 201 and the nominal gear ratio of the metering point 30b ($NGR_{30b}$). The correction signal (u) 201 is an automatic signal provided to compensate for the process disturbances (such as pitch mismatch and a phase correction) described herein above. The correction signal (u) 201 trims the gear ratio (GR) 202 automatically by use of the formula below:

$$GR = \frac{NGR_{50} - u}{NGR_{30b}}$$

The nominal gear ratio (NGR) 205 used by the feedforward control algorithm 203 is comprised of a nominal gear ratio for the pitched unit operation 50 ($NGR_{50}$) and a nominal gear ratio for the metering point 30b ($NGR_{30b}$) which can be calculated by the formula described herein below.

$$NGR = \frac{NGR_{50}}{NGR_{30b}}$$

The nominal gear ratio of the pitched unit operation 50 ($NGR_{50}$) is a constant value, which can be inputted into the gear ratio block (GR) 202 manually by an operator. The $NGR_{50}$ can be calculated as a ratio of the angular velocity of a drive pulley of a pitched unit operation (such as, e.g., a combining unit, a cutting device, an activator, and the like) combining the controlled web 30 with the pitched web 40, and the angular velocity of the motor shaft driving the combining point 50. The formula below shows the calculation of the $NGR_{50}$.

$$NGR_{50} = \frac{\text{Angular velocity pitched unit operation}}{\text{Angular velocity pitched unit operation motor}}$$

The nominal gear ratio of the metering point 30b ($NGR_{30b}$) is a constant value, which can be inputted into the gear ratio block (GR) 202 manually by an operator. The $NGR_{30b}$ can be calculated as a ratio of the angular velocity of a drive pulley of a metering point 30b (a feeding device, such as, e.g., a metering roll, an s-wrap, an omega wrap, a conveyor) metering the controlled web 30, and the angular velocity of the motor shaft driving the metering point 30b. This calculation of the $NGR_{30b}$ also takes into consideration a desired draw or web tension of the controlled web 30 within a particular span of the converter. The formula below shows the calculation of the $NGR_{30b}$.

$$NGR_{30b} = \frac{\text{Angular velocity metering point}}{\text{Angular velocity metering point motor}} * \text{draw}$$

The correction signal (u) 201 can be accomplished by providing the following sequence:

First, the controlled web 30, having pre-produced objects 22, is sensed by a sensor 34 that electronically strobes the encoder 50a. The strobing of the encoder 50a provides an actual position data 50b that is fed to a summing junction 43, wherein the actual position data 50b is compared to a fixed target position constant 44 (as described herein above with respect to the first embodiment), resulting in an error signal 70. The error signal 70 changes when actual position data 50b changes due to the process disturbances described herein above.

Second, the error signal 70 is then fed into a PI (proportional integral) controller 204, which includes a proportional gain (Kp) 71 and an integral gain (Ki) 74. In the PI controller 204, the error signal 70 is converted into the correction signal (u) 201. Thus, the correction signal (u) 201 is based on the error signal 70 (due to the process disturbances described herein above) and the proportional gain (Kp) 71 and the integral gain (Ki) 74. The correction signal (u) 201 can be calculated, once per each pre-produced object 22, by the formula below, wherein, "error" is the error signal 70 and "ΔT" is a time period between consecutive calculations triggered by sensing the pre-produced object 22 on the controlled web 30. "ΔT" is set to a constant value that represents a typical time between products. This way the integral gain of the system is not dependent on the product rate.

$$u = K_p * \text{error} + K_i * \sum \text{error} * \Delta T$$

The calculated herein above servo velocity signal 76 is then fed into a velocity loop servo 78 to adjust a torque signal 79 for controlling the speed of a motor driving the metering point 30b so as to provide registration of the pre-produced objects 22 on the controlled web 30 in relation to the target objects 42 on the target web 40.

SECOND EMBODIMENT

The second embodiment is an exemplary embodiment of the registration control system of the present invention and is shown in FIGS. 5B and 6A. In the second embodiment, the registration control can be provided by the use of a feedforward control method.

FIG. 5B shows a schematic diagram of the process of the second embodiment of registering the pre-produced web of the present invention. In the second embodiment, the registration system is a feedback control system requiring a comparison of an actual position of the pre-produced object 22 on the controlled web 30 to a target object position in relation to the finished product or the pitched unit operation 50. The controlled web 30 is initially fed at a velocity Vo, by a metering point 30b, and the target web 40 is fed to the combining pitched unit operation 50 at a velocity Vt. The actual position data is provided by detection of the position of a pre-produced object 22 of the controlled web 30 moving in the machine direction MD, can occur automatically at a pre-produced object detection stage 33 via a sensor 34 which electronically strobes a resolver 50a providing actual position data 50b of the pre-produced object 22 (see FIG. 6A). Detection of a target object 42 (e.g., diaper core) on the target web 40 moving also in the machine direction MD, can occur at the product detection stage 45 by an operator manually setting the target position constant 44 (see FIG. 6A). The resolver 50a mounted on the pitched unit operation 50 serves as the master reference for the metering point 30b. This master/slaved relationship serves as a feedforward path for the registration system 200 shown in FIG. 6A.

FIG. 6A shows a block diagram of a second embodiment of the registration control system 200 of the present invention. In the registration control system 200, a main reference signal is a converter velocity reference signal 62 of the pitched unit operation 50 that can be provided by an encoder 50a (see FIG. 5B), which provides a change of the converter position reference signal 62 of the encoder 50a over time (for example, one revolution of the encoder 50a per a target object 42). The converter velocity reference signal 62 is equal to the pitch length of the product times the converter rate. The converter velocity reference signal 62 is supplied to a feedforward (FF) control algorithm 203, to be multiplied with a gear ratio (GR) constant 202 in order to produce a servo velocity signal 76, which can be calculated by the formula below:

servo velocity signal=GR*converter velocity reference signal

Alternatively the converter reference signal 62 can be position based and can be used to generate a position based servo signal, utilizing the same control algorithm.

servo position signal=GR*converter position reference signal

The gear ratio (GR) 202 is a ratio of the nominal gear ratio of the pitched unit operation 50 ($NGR_{50}$) trimmed by a correction signal (u) 201 and the nominal gear ratio of the metering point 30b ($NGR_{30b}$). The correction signal (u) 201 is an automatic signal provided to compensate for the process disturbances (such as pitch mismatch and a phase correction) described herein above. The correction signal (u) 201 trims the gear ratio (GR) 202 automatically by use of the formula below:

$$GR = \frac{NGR_{50} - u}{NGR_{30b}}$$

The nominal gear ratio (NGR) 205 used by the feedforward control algorithm 203 is comprised of a nominal gear ratio for the pitched unit operation 50 ($NGR_{50}$) and a nominal gear ratio for the metering point 30b ($NGR_{30b}$), which can be calculated by the formula described herein below.

$$NGR = \frac{NGR_{50}}{NGR_{30b}}$$

The nominal gear ratio of the pitched unit operation 50 ($NGR_{50}$) is a constant value, which can be inputted into the gear ratio block (GR) 202 manually by an operator. The $NGR_{50}$ can be calculated as a ratio of the angular velocity of a drive pulley of a pitched unit operation (such as, e.g., a combining unit, a cutting device, an activator, and the like) combining the controlled web 30 with the pitched web 40, and the angular velocity of the motor shaft driving the combining point 50. The formula below shows the calculation of the $NGR_{50}$.

$$NGR_{50} = \frac{\text{Angular velocity pitched unit operation}}{\text{Angular velocity pitched unit operation motor}}$$

The nominal gear ratio of the metering point 30b ($NGR_{30b}$) is a constant value, which can be inputted into the gear ratio block (GR) 202 manually by an operator. The $NGR_{30b}$ can be calculated as a ratio of the angular velocity of a drive pulley of a metering point 30b (a feeding device, such as, e.g., a metering roll, an s-wrap, an omega wrap, a conveyor) metering the controlled web 30, and the angular velocity of the motor shaft driving the metering point 30b. This calculation of the $NGR_{30b}$ also takes into consideration a desired draw or web tension of the controlled web 30 within a particular span of the converter. The formula below shows the calculation of the $NGR_{30b}$.

$$NGR_{30b} = \frac{\text{Angular velocity metering point}}{\text{Angular velocity metering point motor}} * \text{draw}$$

The correction signal (u) 201 can be accomplished by providing the following sequence:

First, the controlled web 30, having pre-produced objects 22, is sensed by an sensor 34 that electronically strobes the encoder 50*a*. The strobing of the encoder 50*a* provides an actual position data 50*b* that is fed to a summing junction 43, wherein the actual position data 50*b* is compared to a fixed target position constant 44 (as described herein above with respect to the first embodiment), resulting in an error signal 70. The error signal 70 changes when actual position data 50*b* changes due to the process disturbances described herein above.

Second, the error signal 70 is then fed into a PI (proportional integral) controller 204, which includes a proportional gain (Kp) 71 and an integral gain (Ki) 74. In the PI controller 204, the error signal 70 is converted into the correction signal (u) 201. Thus, the correction signal (u) 201 is based on the error signal 70 (due to the process disturbances described herein above) and the proportional gain (Kp) 71 and the integral gain (Ki) 74. The correction signal (u) 201 can be calculated, once per each pre-produced object 22, by the formula below, wherein, "error" is the error signal 70 and "ΔT" is a time period between consecutive calculations triggered by sensing the pre-produced object 22 on the controlled web 30. "ΔT" is set to a constant value that represents a typical time between products. This way the integral gain of the system is not dependent on the product rate.

$$u = K_p * \text{error} + K_i * \sum \text{error} * \Delta T$$

The calculated herein above servo velocity signal 76 is then fed into a velocity loop servo 78 to adjust a torque signal 79 for controlling the speed of a motor driving the metering point 30*b* so as to provide registration of the pre-produced objects 22 on the controlled web 30 in relation to the target objects 42 on the target web 40.

The registration control system 200 of the second embodiment is an exemplary embodiment of the present invention because it improves the performance of the registration control loop 200 by immediately adjusting the servo velocity signal 76 to account for position adjustments to the converter velocity reference signal 62. This occurs automatically because of the feedforward effect of the coupling between the pitched unit operation 50 and the metering point 30*b*. As a result, the disturbance effects described above are minimized when knowledge of the disturbance is used to proactively adjust the control system before the disturbance shows up as errors in the registration of the pre-produced objects 22 of the controlled web 30 in relation to the target objects 42 of the target web 40 or the pitched unit operation 50 (such as, e.g., a combining unit, a cutting device, an activator, and the like).

Referring to FIG. 6A, the registration control structure of the present invention dramatically improves the performance of the registration control system 200 because it makes continuous, instantaneous control adjustments to the controlled web 30. This is different than some registration control schemes where by the registration error has to add up to some finite level before a control correction will be initiated (U.S. Pat. Nos. 5,286,543 and 5,235,515 issued to Ungpiyakul). This improved scheme is implemented via the use of the (PI) registration PI control 204 utilized to generate u 201 to the slave controlled web 30. This (PI) registration controller 204 is unique in the fact the integral term is based on a discrete per pad basis and not a clock time basis. This allows the correction u 201 due to accumulating error to be independent of production speed. While both the pitched unit operation 50 and the controlled web 30 can be controlled with two independent control loops, for many processes it is desirable that the servo velocity signal 76 change when the phase of the pitched unit operation 50 is adjusted relative to the target objects 42 on the target web 40. By using this feedforward control method of the exemplary embodiment, we can effectively change the phase of the pitched unit operation 50 and maintain the proper register of the pre-produced objects 22 on the controlled web 30 without an additional phase adjustment. Further, this feedforward control method of the present invention also can aid in troubleshooting, since this allows separate position adjustments of the pitched unit operation 50 and the target position constant 44 for adjusting the controlled web 30.

Another of the advantages of the current registration control system 200, illustrated in FIG. 6A, over the prior art (for example, U.S. Pat. Nos. 5,286,543 and 5,235,515 issued to Ungpiyakul) is that it utilizes a single processor to simultaneously calculate the registration error 70, provide the master/slave axis positions, and synchronize future control moves for the pitched unit operation 50 and the metering point 30*b*. The advantage of using one central processor for the registration control system 200 is that it eliminates delays and the need for synchronizing multiple processors, which can result in degraded performance of the control system.

THIRD EMBODIMENT

In a third embodiment of the present invention, shown in FIGS. 5C and 6B, the registration control can be provided by use of a machine vision system capable of capturing a pre-produced object 22 in a form of an image.

FIG. 5C shows a schematic diagram of the process of the third embodiment of registering the pre-produced web of the present invention. In the third embodiment, the registration system is a feedback control system requiring a comparison of an actual position of the pre-produced object 22 on the controlled web 30 to a target object position in relation to the finished product or the pitched unit operation 50. The controlled web 30 is initially fed at a velocity Vo, by a metering point 30*b*, the target web 40 is fed to the combining pitched unit operation 50 at a velocity Vt. The actual position data is provided by detection of the position of the pre-produced object 22 of the controlled web 30 moving in the machine direction MD occurs at a pre-produced object detection stage 33 via a machine vision system 302, which is electronically strobed by a signal from a resolver 50*a* working as a position transducer. (It should be noted that while a resolver 50*a* may be used, a machine vision system 302 can be strobed by any suitable position transducer capable of providing a product cycle strobe signal 50*c* (shown in FIG. 6B) corresponding to a product production cycle). For example, the signal 50*c* can be provided from a programmable limit switch (PLS), a photo eye, a proximity sensor of any kind, a programmable logic controller (PLC), or an encoder. The signal 50*c* can be of any frequency corresponding with production cycle of a product, a number of consecutively combined product cycles or a portion of a product cycle.

When the machine vision system 302 receives the product cycle strobe signal 50c, the machine vision system 302 acquires a production image from the controlled web 30 and compares the production image with a reference image, both of which are described below. The machine vision system 302 then calculates an actual error data 306 of the pre-produced object 22 (see FIG. 6B). Similarly, detection of the target object 42 on the target web 40, moving also in the machine direction MD, occurs at the product detection stage 45, for example, manually by an operator setting a target error constant 304 (see FIG. 6B), which is the target position error of the pre-produced object 22, for registering the pre-produced object 22 with the corresponding target object 42.

FIG. 6B shows a block diagram of a third embodiment of the registration control system 300 of the present invention. In the registration control system 300, a main reference signal is a converter velocity reference signal 62 of the pitched unit operation 50 that can be provided by an encoder 50a (see FIG. 5C), which provides a change of the converter position reference signal 62 of the encoder 50a over time (for example, one revolution of the encoder 50a per a target object 42). The converter velocity reference signal 62 is equal to the pitch length of the product times the converter rate. The converter velocity reference signal 62 is supplied to a feedforward (FF) control algorithm 203, to be multiplied with a gear ratio (GR) constant 202 in order to produce a servo velocity signal 76, which can be calculated by the formula below:

servo velocity signal=GR*converter velocity reference signal

Alternatively the converter reference signal 62 can be position based and can be used to generate a position based servo signal, utilizing the same control algorithm.

servo position signal=GR*converter position reference signal

The gear ratio (GR) 202 is a ratio of the nominal gear ratio of the pitched unit operation 50 ($NGR_{50}$) trimmed by a correction signal (u) 201 and the nominal gear ratio of the metering point 30b ($NGR_{30b}$). The correction signal (u) 201 is an automatic signal provided to compensate for the process disturbances (such as pitch mismatch and a phase correction) described herein above. The correction signal (u) 201 trims the gear ratio (GR) 202 automatically by use of the formula below:

$$GR = \frac{NGR_{50} - u}{NGR_{30b}}$$

The nominal gear ratio (NGR) 205 used by the feedforward control algorithm 203 is comprised of a nominal gear ratio for the pitched unit operation 50 ($NGR_{50}$) and a nominal gear ratio for the metering point 30b ($NGR_{30b}$), which can be calculated by the formula described herein below.

$$NGR = \frac{NGR_{50}}{NGR_{30b}}$$

The nominal gear ratio of the pitched unit operation 50 ($NGR_{50}$) is a constant value, which can be inputted into the gear ratio block (GR) 202 manually by an operator. The $NGR_{50}$ can be calculated as a ratio of the angular velocity of a drive pulley of a pitched unit operation (such as, e.g., a combining unit, a cutting device, an activator, and the like) combining the controlled web 30 with the pitched web 40, and the angular velocity of the motor shaft driving the combining point 50. The formula below shows the calculation of the $NGR_{50}$.

$$NGR_{50} = \frac{\text{Angular velocity pitched unit operation}}{\text{Angular velocity pitched unit operation motor}}$$

The nominal gear ratio of the metering point 30b ($NGR_{30b}$) is a constant value, which can be inputted into the gear ratio block (GR) 202 manually by an operator. The $NGR_{30b}$ can be calculated as a ratio of the angular velocity of a drive pulley of a metering point 30b (a feeding device, such as, e.g., a metering roll, an s-wrap, an omega wrap, a conveyor) metering the controlled web 30, and the angular velocity of the motor shaft driving the metering point 30b. This calculation of the $NGR_{30b}$ also takes into consideration a desired draw or web tension of the controlled web 30 within a particular span of the converter. The formula below shows the calculation of the $NGR_{30b}$.

$$NGR_{30b} = \frac{\text{Angular velocity metering point}}{\text{Angular velocity metering point motor}} * \text{draw}$$

The correction signal (u) 201 can be generated by using the following sequence:

First, the controlled web 30, having pre-produced objects 22, is sensed by the machine vision system 302 that receives the product cycle strobe signal 50c, whereupon the machine vision system 302 can capture a production image of the pre-produced object 22 and use a suitable commercially available pattern matching routine, such as, for example, the PatFind™ routine available from Cognex Corp. of Massachusetts, to find and report the difference in the MD direction between the production image and the corresponding reference image as the actual error data 306 that is fed to a summing junction 43, wherein the actual error data 306 is compared to a target error constant 304, which is the desired constant difference in the MD direction between the production image and its corresponding reference image, that can be set by the operator. (It should be noted that the target error constant 304 does not have to be set by the operator. For example, it can be generated automatically by any suitable means such as when a detection system looks at a finished product to determine the target error constant 304 that can register the pre-produced object 22, and provide a new target error constant 304.). The difference between the actual error data 306 and the target error constant 304 results in an error signal 70. The error signal 70 changes when actual error data 306 changes due to the process disturbances described herein above.

Second, the error signal 70 is then fed into a PI (proportional integral) controller 204, which includes a proportional gain (Kp) 71 and an integral gain (Ki) 74. In the PI controller 204, the error signal 70 is converted into the correction signal (u) 201. Thus, the correction signal (u) 201 is based on the error signal 70 (due to the process disturbances described herein above) and the proportional gain (Kp) 71 and the integral gain (Ki) 74. The correction signal (u) 201 can be calculated, once per each pre-produced object 22, by the formula below, wherein, "error" is the error signal 70 and "ΔT" is a time period between consecutive calculations triggered by sensing the pre-produced object 22 on the controlled web 30. "ΔT" is set to a constant value that represents a typical time between products. This way the integral gain of the system is not dependent on the product rate.

$$u = K_p * \text{error} + K_i * \sum \text{error} * \Delta T$$

The calculated herein above servo velocity signal 76 is then fed into a velocity loop servo 78 to adjust a torque signal 79 for controlling the speed of a motor driving the metering point 30b so as to provide registration of the pre-produced objects 22 on the controlled web 30 in relation to the target objects 42 on the target web 40 or the pitched unit operation 50 (such as, e.g., a combining unit, a cutting device, an activator, and the like).

Figure 7:
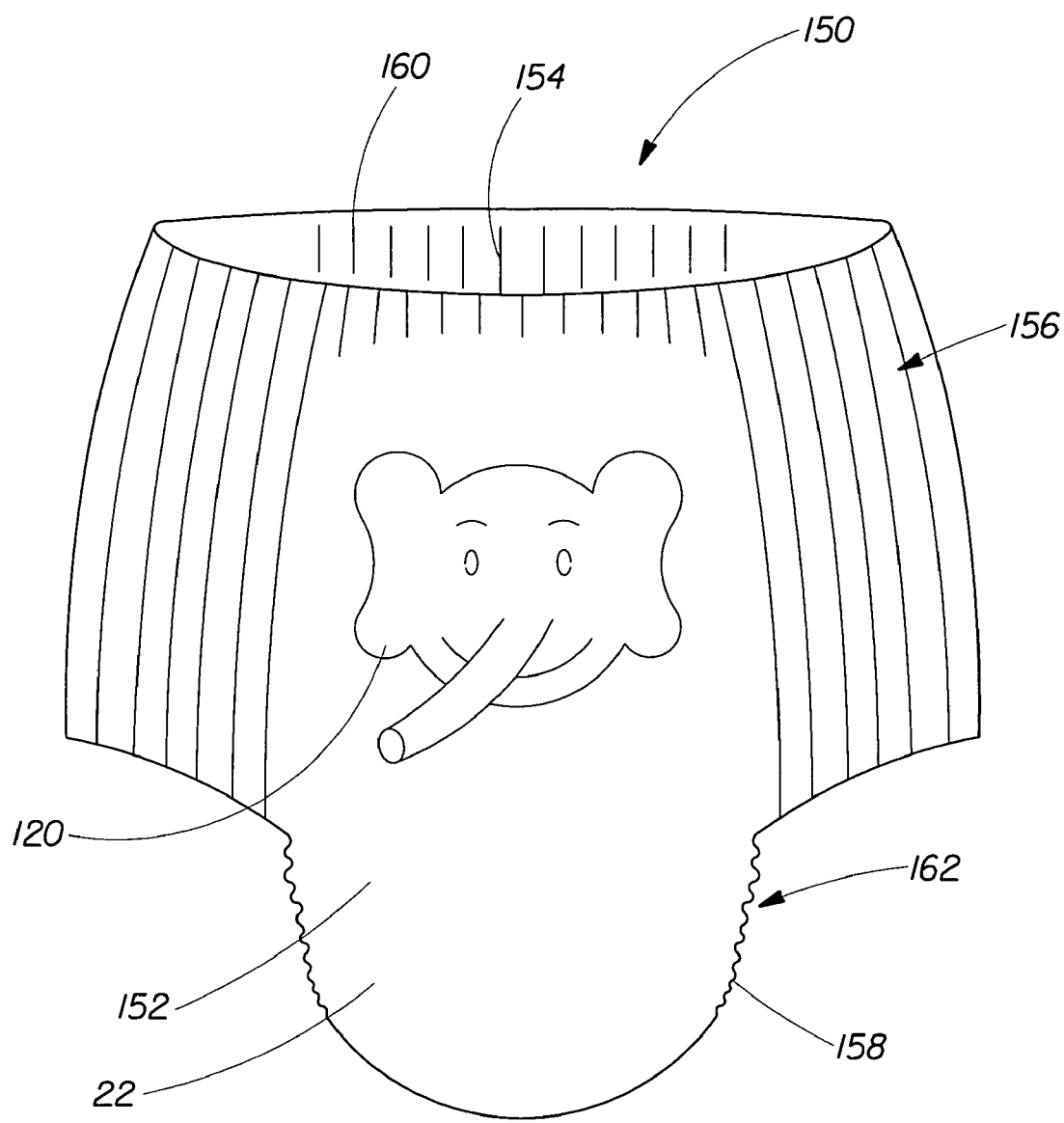
FIG. 7 is a front view of an exemplary embodiment of a disposable absorbent article having registered graphics.
Figure 9A:
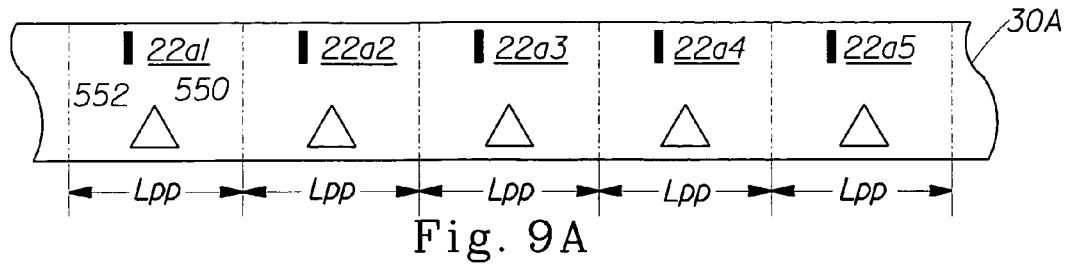
FIGS. 9A, 9B, 9C, 9D and 9E illustrate various embodiments of controlled webs having pre-produced objects.
Figure 9B:
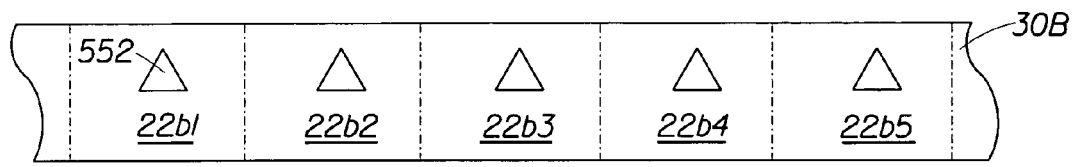
Figure 9C:
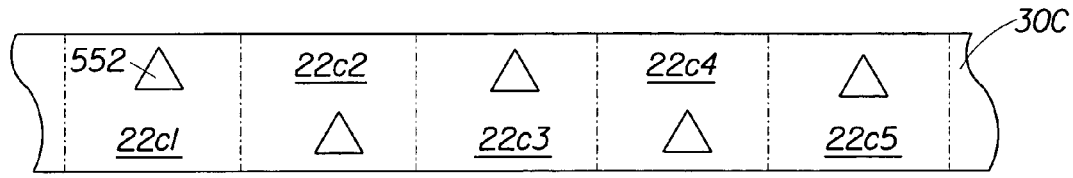
Figure 9D:
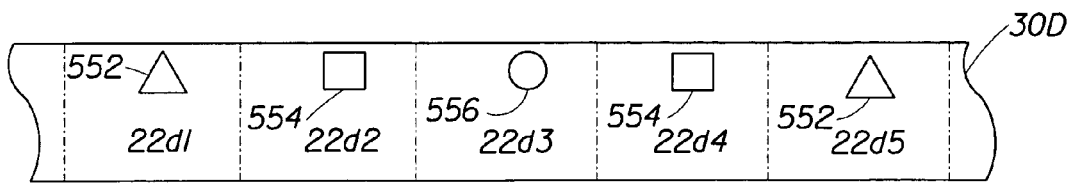
Figure 9E:
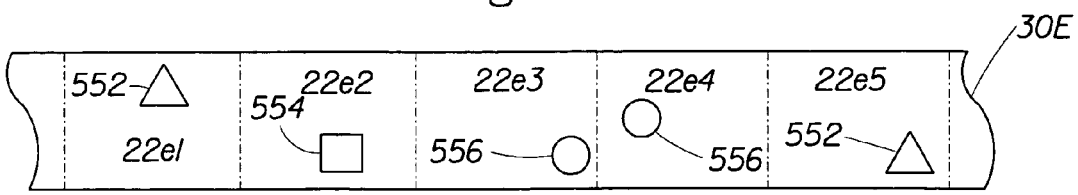
Figure 10:
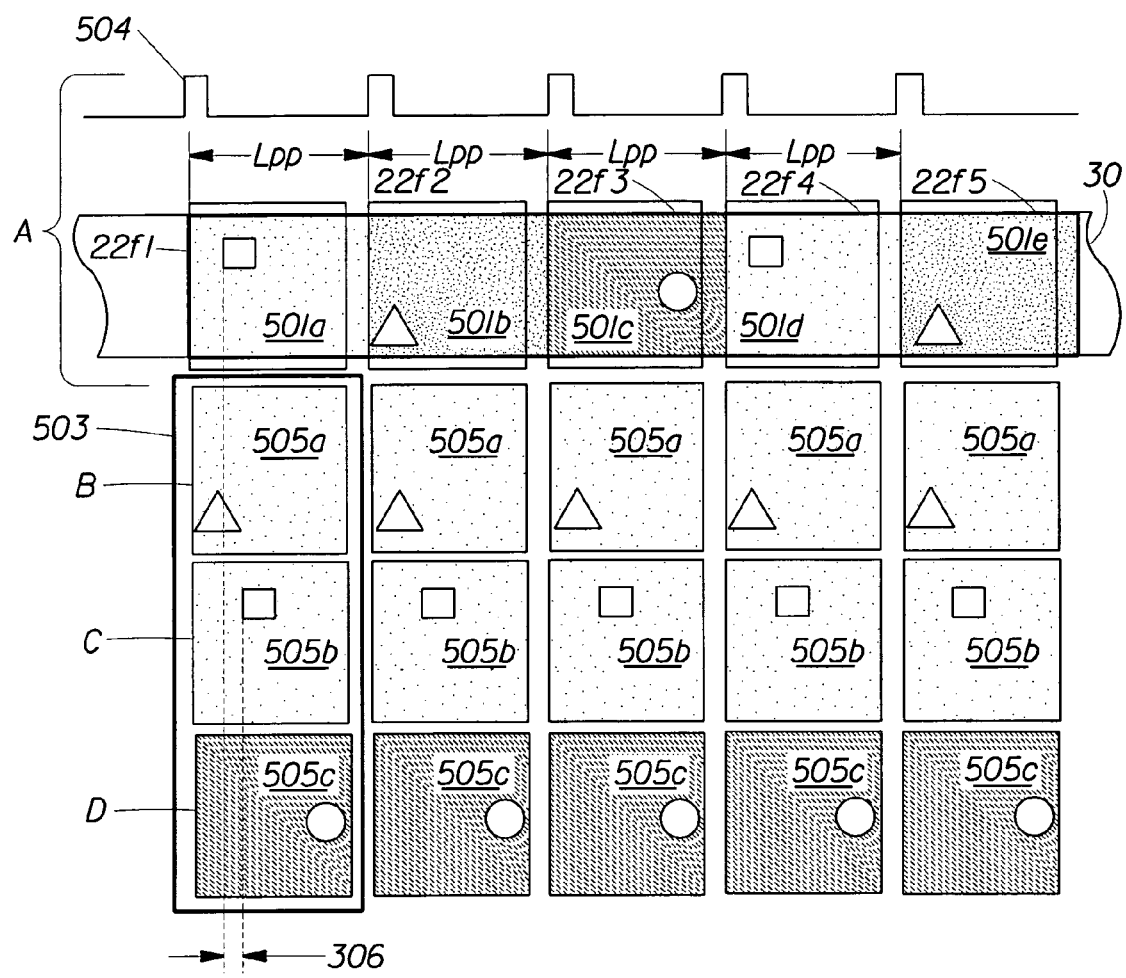
FIG. 10A illustrates a controlled web having pre-produced objects and production images superimposed with the pre-produced objects.
FIGS. 10B, 10C and 10D illustrate stored reference images for comparing with the corresponding production images of FIG. 10A.

FIGS. 9A through 9E show various embodiments of the controlled web 30, denoted as 30A through 30E, respectively. Each embodiment of the controlled web 30 includes a multiplicity of pre-produced objects separated within the controlled web 30 at a product pitch Lpp. Specifically, in FIG. 9A, pre-produced objects 22a1 through 22a5 are identical to each other, and each one includes a registration mark 550 and a graphic 552 in a simplified form of a triangle. (It should be noted that the simplified forms of graphics selected for the examples shown below in FIGS. 9 and 10, are provided as simple geometrical shapes; however, the graphics can be in any complex form, for example, as shown in FIGS. 1, 7 and 8). In FIG. 9B, pre-produced objects 22b1 through 22b5 are identical to each other, and each one includes the graphic 552. In FIG. 9C, pre-produced objects 22c1 and 22c2 are not identical to each other; each one including an identical graphic 552 disposed in a different location within their respective pre-produced objects 22c1 and 22c2. In FIG. 9D, pre-produced objects 22d1, 22d2, and 22d3 are not identical to each other. The pre-produced object 22d1 includes the graphic 552; the pre-produced object 22d2 includes a graphic 554 in a simplified form of a square; and the pre-produced object 22d3 includes a graphic 556 in a simplified form of a circle. The pre-produced objects 22d1, 22d2 and 22d3 can be disposed on the controlled web 30D in any desired order; however, in this embodiment the location of the graphic 552, 554 and 556 is consistent within each of the corresponding pre-produced objects. In FIG. 9E, the pre-produced objects 22e1 through 22e5 are not identical to each other, and each one includes a graphic which is inconsistently located within each corresponding pre-produced object. The pre-produced object 22e1 includes the graphic 552; the pre-produced object 22e2 includes the graphic 554; the pre-produced object 22e3 includes the graphic 556; the pre-produced object 22e4 includes the graphic 556; and the pre-produced object 22e5 includes the graphic 552.

FIG. 10A illustrates a controlled web 30 having pre-produced objects 22 μl through 22f5 and a multiplicity of production images 501a through 501e superimposed with the pre-produced objects. The production images 501a through 501e are captured images by the machine control vision system 302 of the controlled web 30 including one or more pre-produced objects 22f1 through 22f5.

FIGS. 10B, 10C and 10D illustrate stored reference images for comparing with the corresponding production images of FIG. 10A. The logic of the machine vision system 302 captures the production image 501a and compares it to a set of multiple stored reference images 503 comprising the stored images 505a, 505b, and 505c, in order to produce an actual error data 306. (It should be noted that although the example shows three stored images, the number of stored images can be any suitable number.) To obtain the actual error data 306, the machine vision system 302 first compares the production image 501a to the set of multiple stored reference images 503 comprising the stored images 505a, 505b, and 505c, looking for a match, within threshold limits. Secondly, upon finding a match, for example 505b, the machine vision system 302 is capable to measure the differences both in the machine direction and in the cross machine direction, as well as indicating the degree to which the production image 501a matches the stored reference image 505b. With respect to the registration control system 300 of the present invention, the difference in machine direction between the production image 501a and the stored reference image 503b is then transmitted as the actual error data 306. The actual error data 306 can be transmitted in a multiple number of ways, commonly known in the art, for example, as a proportional analog voltage, a proportional current signal, or as a digital number. The machine vision system 302 can repeat this actual error data calculation and transmission to the registration control system 300 for each production image (501b, 501c, 501d, 501e and the like) for each product cycle strobe signal 50c.

It is common in the art to register a controlled web 30, using registration marks 550 or edges (as shown in patent U.S. Pat. No. 5,359,525) that are identical in shape and location for every pre-produced object 22a1–22a5 on the controlled web 30A (FIG. 9A). An advantage that the third embodiment of the invention as described above has over the current art is that the controlled web 30 can be registered without the use of a registration mark 550. Neither do the pre-produced objects (e.g.: 22e1–22e5 in FIG. 9E) need to be identical. In addition, the controlled web 30 can be registered regardless of the order of pre-produced objects 22b1–22e5 (See FIGS. 9B–9E) on the controlled web 30.

FOURTH EMBODIMENT

Figure 6C:
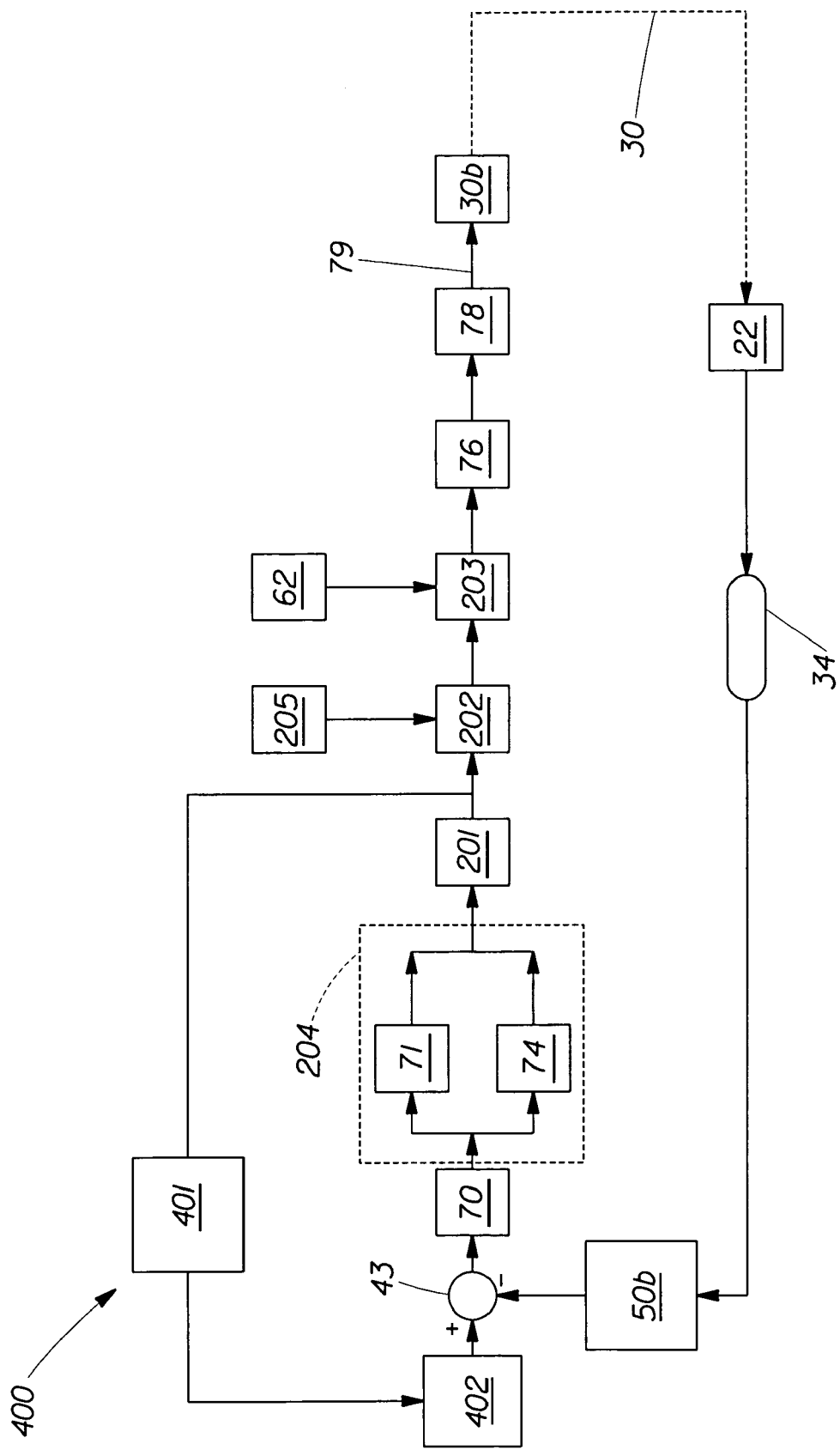
FIG. 6C is a block diagram of the fourth embodiment of the registration control system of the present invention.

Referring now to FIG. 6C, an exemplary fourth embodiment of a registration control system 400 is shown. Said registration control system 400 may be used in a multitude of processes, particularly the process depicted in FIG. 5B. In this fourth embodiment, the registration control can be provided by the use of a feedforward control method and automatic phasing control method. Additionally, this fourth embodiment may prove especially useful when a combination of random errors and accumulating errors are present such that said combination causes an offset around the target position 402 (e.g., process for applying landing zones to a disposable diaper).

FIG. 5B shows a schematic diagram of the process of the fourth embodiment of registering the pre-produced web of the present invention. In the fourth embodiment, the registration system is a feedback control system requiring a comparison of an actual position of the pre-produced object 22 on the controlled web 30 to a target object position in relation to the finished product or the pitched unit operation 50. The controlled web 30 is initially fed at a velocity Vo, by a metering point 30b, and the target web 40 is fed to the combining pitched unit operation 50 at a velocity Vt. The actual position data is provided by detection of the position of a pre-produced object 22 of the controlled web 30 moving in the machine direction MD, can occur automatically at a pre-produced object detection stage 33 via a sensor 34 which electronically strobes a resolver 50a providing actual position data 50b of the pre-produced object 22 (see FIG. 6C). Detection of a target object 42 (e.g., diaper core) on the target web 40 moving also in the machine direction MD, can occur at the product detection stage 45 by an operator manually setting the target position and automatically phased (see FIG. 6C). The resolver 50a mounted on the pitched unit operation 50 serves as the master reference for the metering point 30b. This master/slave relationship serves as a feedforward path for the registration system 400 shown in FIG. 6C.

FIG. 6C shows a block diagram of a fourth embodiment of the registration control system 400 of the present invention. In the registration control system 400, a main reference signal is a converter velocity reference signal 62 of the pitched unit operation 50 that can be provided by an encoder 50a (see FIG. 5B), which provides a change of the converter position reference signal 62 of the encoder 50a over time (for example, one revolution of the encoder 50a per a target object 42). The converter velocity reference signal 62 is equal to the pitch length of the product times the converter rate. The converter velocity reference signal 62 is supplied to a feedforward (FF) control algorithm 203, to be multiplied with a gear ratio (GR) constant 202 in order to produce a servo velocity signal 76, which can be calculated by the formula below:

servo velocity signal=GR*converter velocity reference signal

Alternatively the converter reference signal 62 can be position based and can be used to generate a position based servo signal, utilizing the same control algorithm.

servo position signal=GR*converter position reference signal

The gear ratio (GR) 202 is a ratio of the nominal gear ratio of the pitched unit operation 50 ($NGR_{50}$) trimmed by a correction signal (u) 201 and the nominal gear ratio of the metering point 30b ($NGR_{30b}$). The correction signal (u) 201 is an automatic signal provided to compensate for the process disturbances (such as pitch mismatch and a phase correction) described herein above. The correction signal (u) 201 trims the gear ratio (GR) 202 automatically by use of the formula below:

$$GR = \frac{NGR_{50} - u}{NGR_{30b}}$$

The correction signal (u) 201 changes the automatic target position phase 401 automatically by use of the formula below:

$$\text{Target}(n) = (\text{Target}(n-1) + -x) \text{IF} \frac{u(1) + \ldots u(rs)}{(rs)} <> \text{threshold}$$

The nominal gear ratio (NGR) 205 used by the feedforward control algorithm 203 is comprised of a nominal gear ratio for the pitched unit operation 50 ($NGR_{50}$) and a nominal gear ratio for the metering point 30b ($NGR_{30b}$), which can be calculated by the formula described herein below.

$$NGR = \frac{NGR_{50}}{NGR_{30b}}$$

The nominal gear ratio of the pitched unit operation 50 ($NGR_{50}$) is a constant value, which can be inputted into the gear ratio block (GR) 202 manually by an operator. The $NGR_{50}$ can be calculated as a ratio of the angular velocity of a drive pulley of a pitched unit operation (such as, e.g., a combining unit, a cutting device, an activator, and the like) combining the controlled web 30 with the pitched web 40, and the angular velocity of the motor shaft driving the combining point 50. The formula below shows the calculation of the $NGR_{50}$.

$$NGR_{50} = \frac{\text{Angular velocity pitched unit operation}}{\text{Angular velocity pitched unit operation motor}}$$

The nominal gear ratio of the metering point 30b ($NGR_{30b}$) is a constant value, which can be inputted into the gear ratio block (GR) 202 manually by an operator. The $NGR_{30b}$ can be calculated as a ratio of the angular velocity of a drive pulley of a metering point 30b (a feeding device, such as, e.g., a metering roll, an s-wrap, an omega wrap, a conveyor) metering the controlled web 30, and the angular velocity of the motor shaft driving the metering point 30b. This calculation of the $NGR_{30b}$ also takes into consideration a desired draw or web tension of the controlled web 30 within a particular span of the converter. The formula below shows the calculation of the $NGR_{30b}$.

$$NGR_{30b} = \frac{\text{Angular velocity metering point}}{\text{Angular velocity metering point motor}} * \text{draw}$$

The correction signal (u) 201 can be accomplished by providing the following sequence:

First, the controlled web 30, having pre-produced objects 22, is sensed by an sensor 34 that electronically strobes the encoder 50a. The strobing of the encoder 50a provides an actual position data 50b that is fed to a summing junction 43, wherein the actual position data 50b is compared to a fixed target position constant 44 (as described herein above with respect to the first embodiment), resulting in an error signal 70. The error signal 70 changes when actual position data 50b changes due to the process disturbances described herein above.

Second, the error signal 70 is then fed into a PI (proportional integral) controller 204, which includes a proportional gain (Kp) 71 and an integral gain (Ki) 74. In the PI controller 204, the error signal 70 is converted into the correction signal (u) 201. Thus, the correction signal (u) 201 is based on the error signal 70 (due to the process disturbances described herein above) and the proportional gain (Kp) 71 and the integral gain (Ki) 74. The correction signal (u) 201 can be calculated, once per each pre-produced object 22, by the formula below, wherein, "error" is the error signal 70 and "ΔT" is a time period between consecutive calculations triggered by sensing the pre-produced object 22 on the controlled web 30. "ΔT" is set to a constant value that represents a typical time between products. This way the integral gain of the system is not dependent on the product rate.

$$u = K_p * \text{error} + K_i * \sum \text{error} * \Delta T$$

The calculated herein above servo velocity signal 76 is then fed into a velocity loop servo 78 to adjust a torque signal 79 for controlling the speed of a motor driving the metering point 30b so as to provide registration of the pre-produced objects 22 on the controlled web 30 in relation to the target objects 42 on the target web 40.

The calculated herein correction signal 201 is then fed into filter/pulse generator 401 to determine if a bias in data has occurred around the target position 402 then to generate a small (+−1 mm) correction to the target position 402 resulting in phase change to it.

Advantages of the current registration control system 400, illustrated in FIG. 6C, over the prior art (for example, U.S. Pat. Nos. 5,286,543 and 5,235,515 issued to Ungpiyakul) is that it utilizes a single processor to simultaneously calculate the registration error 70, provide the master/slave axis positions, synchronize future control moves for the pitched unit operation 50 and the metering point 30b and automatically phase the target position 402. The advantage of phasing the target position is that it automatically compensates the setpoint to account for physical separation between the sensor and the pitched unit operation. The advantage of using one central processor for the registration control system 400 is that it eliminates delays and the need for synchronizing multiple processors, which can result in degraded performance of the control system and saves hardware cost for buying addition optics, sensors, et. for additional controls needed to accomplish these functions.

FIFTH EMBODIMENT

Figure 5D:
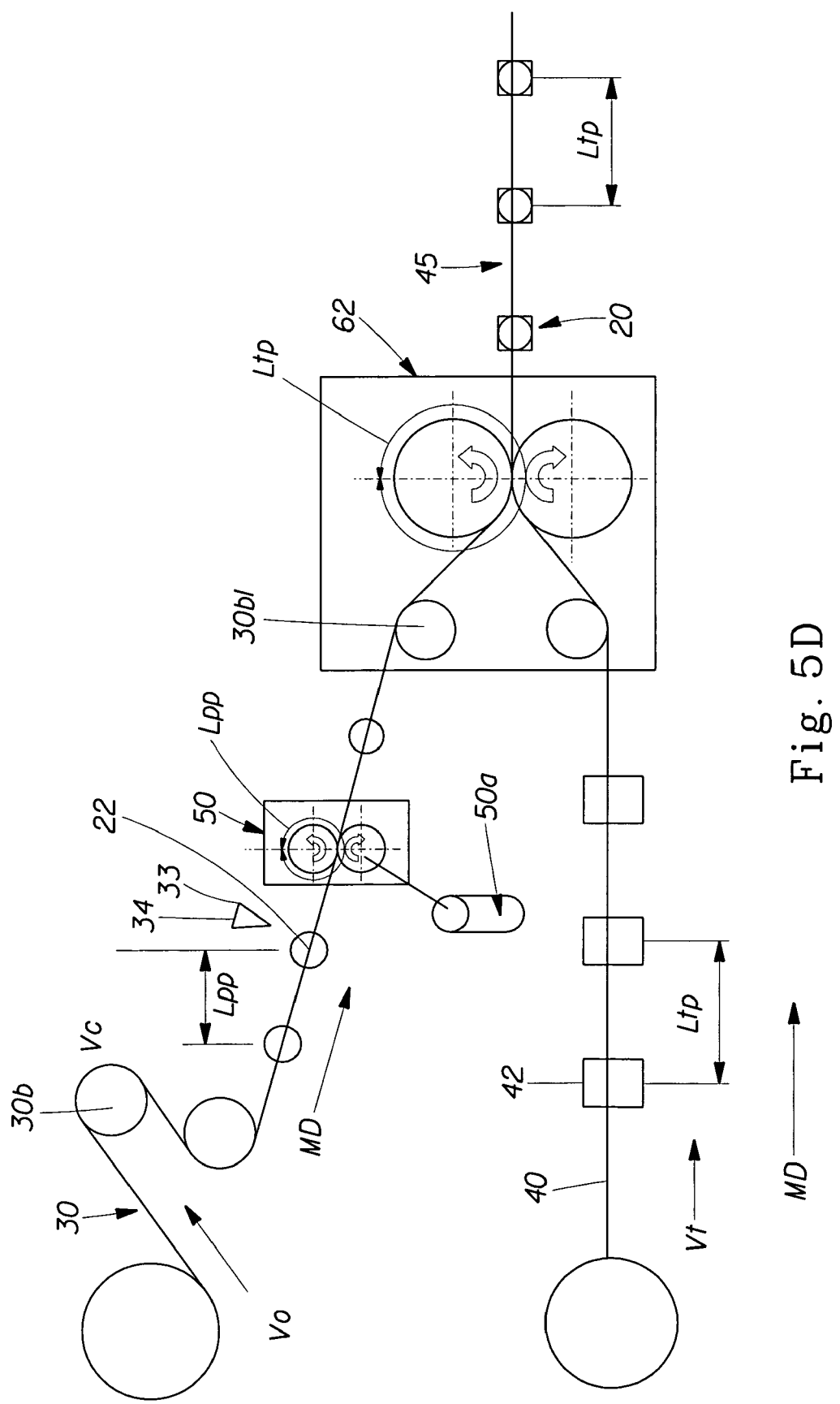
FIG. 5D is a schematic diagram of a fifth embodiment of the present invention showing the process of combining two simultaneously advancing webs.
Figure 6D:
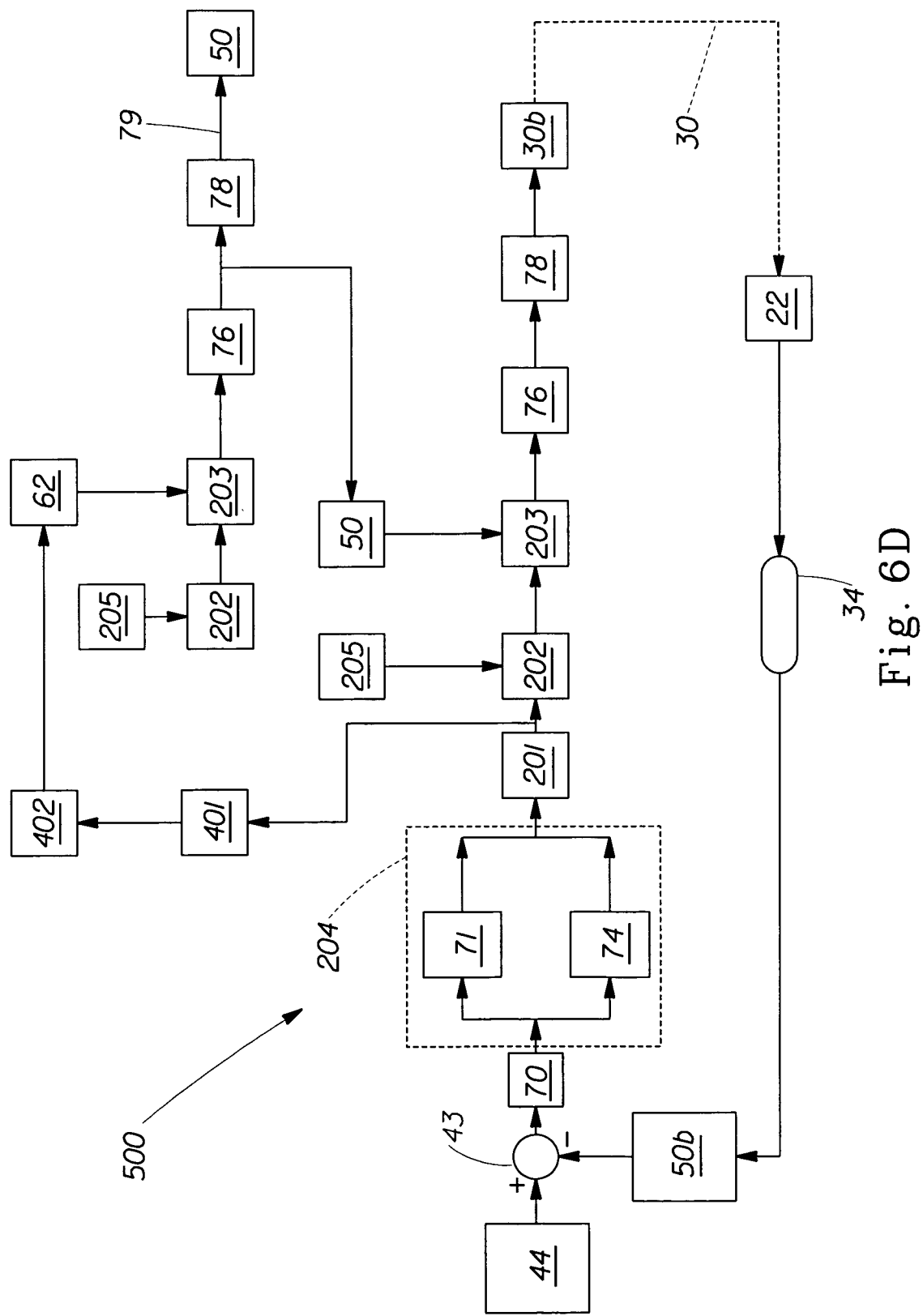
FIG. 6D is a block diagram of the fifth embodiment of the registration control system of the present invention.

Referring now to FIG. 6D, an exemplary fifth embodiment of a registration control system 500 is shown. Said registration control system 500 may be used in a multitude of processes, particularly the process depicted in FIG. 5D. In this fifth embodiment, the registration control can be provided by the use of a feedforward control method and automatic phasing control method. Additionally, this fifth embodiment may prove especially useful when random errors and accumulating errors are present and when the process includes multiple pitched unit operations on a single web (e.g., a first pitched unit operation 50 is used to slit a diaper ear web into two separate webs and a second pitched unit operation 62 is used to cut said webs into discrete parts for subsequent application onto another web). Additionally, this fifth embodiment may prove especially useful when it is desired to keep the tension of control web 30 constant.

FIG. 5D shows a schematic diagram of the process of the fifth embodiment of registering the pre-produced web of the present invention. In the fifth embodiment, the registration system is a feedback control system requiring a comparison of an actual position of the pre-produced object 22 on the controlled web 30 to a target object position in relation to the finished product or the pitched unit operation 50. The controlled web 30 is initially fed at a velocity Vo, by a metering point 30b, and the target web 40 is fed to the combining pitched unit operation 50 at a velocity Vt. The actual position data is provided by detection of the position of a pre-produced object 22 of the controlled web 30 moving in the machine direction MD, can occur automatically at a pre-produced object detection stage 33 via a sensor 34 which electronically strobes a resolver 50a providing actual position data 50b of the pre-produced object 22 (see FIG. 6D). Detection of a target object 42 (e.g., diaper core) on the target web 40 moving also in the machine direction MD, can occur at the product detection stage 45 by an operator manually setting the target position constant 44 (see FIG. 6D). The resolver 50a mounted on the pitched unit operation 50 serves as the master reference for the metering points 30b and 30b1. This master/slave relationship serves as a feedforward path for the registration system 500 shown in FIG. 6D. Such a relationship allows for the maintaining of constant web tension, if desired.

FIG. 6D shows a block diagram of a fifth embodiment of the registration control system 500 of the present invention. In the registration control system 500, a main reference signal is a converter velocity reference signal 62 of the pitched unit operation 50 that can be provided by an encoder 50a (see FIG. 5D), which provides a change of the converter position reference signal 62 of the encoder 50a over time (for example, one revolution of the encoder 50a per a target object 42). The converter velocity reference signal 62 is equal to the pitch length of the product times the converter rate. The converter velocity reference signal 62 is supplied to a feedforward (FF) control algorithm 203, to be multiplied with a gear ratio (GR) constant 202 in order to produce a servo velocity signal 76, which can be calculated by the formula below:

servo velocity signal=$GR$*converter velocity reference signal

Alternatively the converter reference signal 62 can be position based and can be used to generate a position based servo signal, utilizing the same control algorithm.

servo position signal=$GR$*converter position reference signal

The gear ratio (GR) 202 is a ratio of the nominal gear ratio of the pitched unit operation 50 ($NGR_{50}$) trimmed by a correction signal (u) 201 and the nominal gear ratio of the metering points 30b ($NGR_{30b}$) and 30b1 ($NGR_{30b1}$). The correction signal (u) 201 is an automatic signal provided to compensate for the process disturbances (such as pitch mismatch and a phase correction) described herein above. The correction signal (u) 201 trims the gear ratio (GR) 202 automatically by use of the formulas below:

$$GR = \frac{NGR_{50} - u}{NGR_{30b}} \text{ and } GR = \frac{NGR_{50} - u}{NGR_{30b1}}$$

The correction signal (u) 201 changes automatically the pitched unit-op 50 position phase 401 automatically by use of the formula below:

TargetPhaseOffset$(n)$=$(u(n)*Kff)IF$(filtered|$u(n)-u(n-1)$|>threshold)

The nominal gear ratio (NGR) 205 used by the feedforward control algorithm 203 is comprised of a nominal gear ratio for the pitched unit operation 50 ($NGR_{50}$) and a nominal gear ratio for the metering points 30b ($NGR_{30b}$) and 30b1 ($NGR_{30b1}$), which can be calculated by the formulas described herein below.

$$NGR = \frac{NGR_{50}}{NGR_{30b}} \text{ and } NGR = \frac{NGR_{50}}{NGR_{30b1}}$$

The nominal gear ratio of the pitched unit operation 50 (NGR$_{50}$) is a constant value, which can be inputted into the gear ratio block (GR) 202 manually by an operator. The NGR$_{50}$ can be calculated as a ratio of the angular velocity of a drive pulley of a pitched unit operation (such as, e.g., a combining unit, a cutting device, an activator, and the like) combining the controlled web 30 with the pitched web 40, and the angular velocity of the motor shaft driving the combining point 50. The formula below shows the calculation of the NGR$_{50}$.

$$NGR_{50} = \frac{\text{Angular velocity pitched unit operation}}{\text{Angular velocity pitched unit operation motor}}$$

The nominal gear ratio of the metering points 30*b* (NGR$_{30b}$) and 30*b*1 (NGR$_3$Obi) are constant values, which can be inputted into the gear ratio block (GR) 202 manually by an operator. The NGR$_{30b}$ and NGR$_{30b1}$ can be calculated as a ratio of the angular velocity of a drive pulley of a metering points 30*b* and 30*b*1 (feeding devices, for example, a metering roll, an s-wrap, an omega wrap, a conveyor) metering the controlled web 30, and the angular velocity of the motor shaft driving the metering points 30*b* and 30*b*1. This calculation of the NGR$_{30b}$ and NGR$_{30b1}$ also takes into consideration a desired draw or web tension of the controlled web 30 within a particular span of the converter. The formulas below shows the calculation of the NGR$_{30b}$ and NGR$_{30b1}$.

$$NGR_{30b} = \frac{\text{Angular velocity metering point}}{\text{Angular velocity metering point motor}} * \text{draw}$$

$$NGR_{30b1} = \frac{\text{Angular velocity metering point}}{\text{Angular velocity metering point motor}} * \text{draw}$$

The correction signal (u) 201 can be accomplished by providing the following sequence:

First, the controlled web 30, having pre-produced objects 22, is sensed by an sensor 34 that electronically strobes the encoder 50*a*. The strobing of the encoder 50*a* provides an actual position data 50*b* that is fed to a summing junction 43, wherein the actual position data 50*b* is compared to a fixed target position constant 44 (as described herein above with respect to the first embodiment), resulting in an error signal 70. The error signal 70 changes when actual position data 50*b* changes due to the process disturbances described herein above.

Second, the error signal 70 is then fed into a PI (proportional integral) controller 204, which includes a proportional gain (Kp) 71 and an integral gain (Ki) 74. In the PI controller 204, the error signal 70 is converted into the correction signal (u) 201. Thus, the correction signal (u) 201 is based on the error signal 70 (due to the process disturbances described herein above) and the proportional gain (Kp) 71 and the integral gain (Ki) 74. The correction signal (u) 201 can be calculated, once per each pre-produced object 22, by the formula below, wherein, "error" is the error signal 70 and "ΔT" is a time period between consecutive calculations triggered by sensing the pre-produced object 22 on the controlled web 30. "ΔT" is set to a constant value that represents a typical time between products. This way the integral gain of the system is not dependent on the product rate.

$$u = K_p * \text{error} + K_i * \sum \text{error} * \Delta T$$

The calculated herein above servo velocity signal 76 is then fed into a velocity loop servo 78 to adjust a torque signal 79 for controlling the speed of a motor driving the metering points 30*b* and 30*b*1 so as to provide registration of the pre-produced objects 22 on the controlled web 30 in relation to the target objects 42 on the target web 40.

The calculated herein correction signal 201 is then fed into filter 401. If the value has changed by more than a pre-determined threshold since the last correction, the gear ratio 201 is multiplied by a feedforward gain 401 to calculate the new target phase offset 402. The feedforward gain is static, but is predetermined as a function of the physical separation between the sensor 34 and the pitched Unit-Op 50.

One advantage of the current registration control system 500, illustrated in FIG. 6D, over the prior art (for example, U.S. Pat. Nos. 5,286,543 and 5,235,515 issued to Ungpiyakul) is that it utilizes a single processor to simultaneously calculate the registration error 70, provide the master/slave axis positions, synchronize future control moves for the pitched unit operation 50 and the metering points 30*b* and 30*b*1 and automatically phase the pitched unit operation 50. An advantage of automatically phasing the pitched unit operation 50 is that an additional phasing control loop and sensor is unnecessary at that operation. An advantage of using one central processor for the registration control system 500 is that it eliminates delays and the need for synchronizing multiple processors, which can result in degraded performance of the control system and saves hardware cost for buying addition optics, sensors, et. for additional controls needed to accomplish these functions.

Another advantage of the current registration control system is that constant web tension may be achieved. One exemplary, non-limiting method for achieving constant web tension is to control the gear ratio of all the metering points while phasing a pitched unit operation and changing the feed rate of the controlled web. One such benefit of having constant web tension is that the manufacturing process is more stable over a range of pre-produced web pitch.

ALL EMBODIMENTS

Previous design efforts targeting registered graphics have been based upon separate control systems for incoming graphics pitch length correction and phase position control. However, the system of the present invention incorporates simultaneous correction based upon the relationship between pitch length and the velocity. It will be understood by those of skill in the art that position has an integral relationship to velocity and can therefore be controlled using the same system that controls velocity.

Disposable diaper products typically include a topsheet material, an absorbent core, and a backsheet material. The topsheet material is located to be placed facing the body or nearest the body when the diaper is worn and is generally provided with a liquid permeable region so that body exudates can flow through the topsheet to the absorbent core, where they are contained. The backsheet material, which is placed away from the body during wear, is typically liquid impermeable so that outer clothing or other articles such as bedsheets are not wetted by the body exudates. Such an exemplary diaper is disclosed in, for example, Buell U.S. Pat. No. 5,569,234, directed to a "Disposable Pull-on Pant".

In addition to the basic topsheet, core, and backsheet components, it will be understood by those of skill in the art that many other features for disposable absorbent articles are within the scope of the present invention. For example, barrier cuffs as described in Lawson and Dragoo U.S. Pat. Nos. 4,695,278 and 4,795,454 are a desirable feature for disposable absorbent articles. In addition, skin care type topsheets that are provided with lotion thereon for the purpose of reducing skin irritation and chafing are a desirable feature herein.

Referring to FIG. 7, there is shown an exemplary disposable pull-on diaper 150, which is generally pulled onto the body of the wearer by inserting the legs into the leg openings 162 and pulling the article up over the waist. Generally, "pull-on diaper" refers to pull-on garments worn by small children and other incontinent individuals to absorb and contain body exudates. It should be understood that other pull-on garments such as training pants, incontinent briefs, feminine briefs, feminine hygiene garments or panties, and like, are included herein.

Referring to FIGS. 7 and 8, the diaper 150 is generally comprised of a backsheet 152, a topsheet 154 and an absorbent layer 156 (shown in dashed lines in FIG. 8) located between the backsheet 152 and the topsheet 154. The backsheet 154 is the surface which faces away from the wearer's body, while the topsheet 152 is the surface which faces toward the wearer's body. In one embodiment of the present invention, the backsheet 152 is comprised of at least a microporous polymer film printed with pre-produced objects 22 (e.g. graphics 120, 122) as described herein. The backsheet 152 may further comprise a layer of nonwoven material (see reference numeral 32, FIGS. 4A, B) laminated or otherwise secured to the microporous film layer, in which case there is provided a more cloth-like and garment-like feel. In such a case, the nonwoven web may be fed to the web handling process as a continuous incoming web and may be combined in a desired relationship with the controlled web 30 and the target web 40.

In the case of a laminated nonwoven backsheet, it is desirable that the surface texture of the non-woven not be impacted by a laminated sublayer, e.g. a microporous polymer film sublayer, which pulls it back and causes it to "pucker." It is more desirable that any puckering that is required for the operation of a registration system be limited to the underlying polymer material, which is neither seen nor felt by the user of the product, see FIG. 4B. The system of the present invention can be used in cases where the pitch length Lpp of the microporous film web (controlled web 30) may be longer or shorter than that of the product, Ltp. Overfeeding the target web may lead to superior surface texture. After the final cut, when Lpp is less than Ltp, the film material pulls back the nonwoven material that forms part of the product. This creates a roughened texture of the exposed surface of the laminates where the consumer can see and feel. This, when Lpp is greater than Ltp, the impact of the unequal combining upon which the registration systems depends is hidden from the consumer. In general, Lc should be greater than both Lpp and Ltp, to avoid the possibility of a zero-tension situation.

Elastically extensible side panels 156 are provided to ensure more comfortable and contouring fit by initially conformably fitting the pull-on diaper 150 to the wearer and sustaining this fit throughout the time of wear well past when it has been loaded with exudates. Leg elastics 158 and waist elastic region 160 are also provided to enhance the fit around the legs and waist, respectively.

FIG. 7 shows the front view of the diaper 150 with an exemplary pre-produced object 22, graphic 120 positioned in about the upper region of the backsheet, on the back side of the diaper 150. In FIG. 8, there is shown a simplified plan view of an embodiment of a disposable absorbent article in its flat, uncontracted state prior to formation pre-produced object 22, graphic 120 is shown in the back region of the diaper with graphic 122 additionally shown in the front region of the diaper.

It is understood that the examples and embodiments described herein are for illustrative purposes only and that various modifications or changes in light thereof will be suggested to one of skill in the art without departing from the scope of the present invention.

All documents cited in the detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for registering an off-line produced web having pre-produced objects longitudinally spaced at a pitch interval to a converting line manufacturing disposable absorbent articles, such as diapers, pull-ups, feminine hygiene articles, and the like, or a component of a disposable absorbent article, the off-line produced web being manipulated as a controlled web in order for the pre-produced object of the controlled web to be registered in relation to a target bias position and in control automatically with the pitched unit operation, and automatically phase the target position bias, the method comprising the steps of:

a. providing a controlled web having pre-produced objects spaced at a controlled pitch interval, wherein the controlled web being provided at a controlled velocity in a machine direction;

b. providing an actual bias position of the pre-produced object on the controlled web by detecting the pre-produced object with a sensor within a manufacturing cycle of a pitched unit operation;

c. providing a target bias position constant at a desired position within a manufacturing cycle of the pitched unit operation;

d. generating a correction signal based upon the actual bias position data and the target bias position constant;

e. adjusting the controlled velocity of the controlled web in order to register the pre-produced object of the controlled web in relation to the target bias position constant;

f. coupling the pitched unit operation with a controlled web metering point by providing a converter position reference signal fed forward from the pitched unit operation functioning as an independent axis to the controlled web metering point functioning as a dependent axis in order for the pre-produced object of the controlled web be in phase automatically with the pitched unit operation; and g. adjusting the target position in order to phase the actual position based on the controlled web bias.

2. A method for registering an off-line produced web having pre-produced objects longitudinally spaced at a pitch interval to a converting line manufacturing disposable absorbent articles, such as diapers, pull-ups, feminine hygiene articles, and the like, or a component of a disposable absorbent article, the off-line produced web being manipulated as a controlled web in order for the pre-produced object of the controlled web to be registered in relation to a target bias position and in control automatically with a first pitched unit operation and automatically phase the first pitched unit operation in order to maintain phase of the pre-produced web with a second pitched unit operation, the method comprising the steps of;

a. providing a controlled web having pre-produced objects spaced at a controlled pitch interval, wherein the controlled web being provided at a controlled velocity in a machine direction;

b. providing an actual bias position of the pre-produced object on the controlled web by detecting the pre-produced object with a sensor within a manufacturing cycle of a pitched unit operation;

c. providing a target bias position constant at a desired position within a manufacturing cycle of the first pitched unit operation;

d. generating a correction signal based upon the actual bias position data and the target bias position constant;

e. adjusting the controlled velocity of the controlled web in order to register the pre-produced object of the controlled web in relation to the target bias position constant;

f. coupling the first pitched unit operation with at least one controlled web metering point by providing a converter position reference signal fed forward from the second pitched unit operation functioning as an independent axis to the controlled web metering point functioning as a dependent axis in order for the pre-produced object of the controlled web be in phase automatically with the first pitched unit operation;

g. inferring the pre-produced object pitch from the registration control loop output and using feedforward gain to automatically adjust a target phase offset position of the second pitched unit operation in order to compensate for variations in the pre-produced object pitch and to maintain the proper phase relationship.

3. The method of claim 2 wherein the first pitched unit operation is used to slit a diaper ear web into two separate webs and the second pitched unit operation is used to cut said webs into discrete parts for subsequent application onto another web.

4. The method of claim 3 wherein the diaper ear web is processed at a constant web tension.

5. The method of claim 1 wherein the controlled web is processed at a constant web tension.

6. The method of claim 2 wherein the controlled web is processed at a constant web tension.

* * * * *

UNITED STATES PATENT AND TRADEMARK OFFICE
CERTIFICATE OF CORRECTION

PATENT NO. : 6,957,160 B2 Page 1 of 1
APPLICATION NO. : 10/731807
DATED : October 18, 2005
INVENTOR(S) : Charles Phillip Miller et al.

It is certified that error appears in the above-identified patent and that said Letters Patent is hereby corrected as shown below:

Column 6,
Line 18, delete "device;" and insert -- device, --.

Column 7,
Line 14, delete "tern" and insert -- term --.
Line 63, delete "FIG." and insert -- FIGS.--.

Column 21,
Line 62, delete "22 µl" and insert -- 22$fl$ --.

Column 27,
Line 18, delete "(NGR$_3$Obi)" and insert -- (NGR$_{30b1}$) --.

Column 31,
Line 13, delete "steps of;" and insert -- steps of: --.

Signed and Sealed this

Twentieth Day of June, 2006

JON W. DUDAS
*Director of the United States Patent and Trademark Office*